United States Patent [19]
Blaser et al.

[11] Patent Number: 5,527,678
[45] Date of Patent: Jun. 18, 1996

[54] CAGB AND CAGC GENES OF HELICOBACTER PYLORI AND RELATED COMPOSITIONS

[75] Inventors: Martin J. Blaser; Murali K. R. Tummuru; Smita A. Sharma, all of Nashville, Tenn.

[73] Assignee: Vanderbilt University, Nashville, Tenn.

[21] Appl. No.: 327,494

[22] Filed: Oct. 21, 1994

[51] Int. Cl.$^6$ ............................... C12Q 1/68; C12P 19/34
[52] U.S. Cl. .......................... 435/6; 435/91.2; 536/23.1; 536/24.32
[58] Field of Search ...................... 435/6, 91.2, 320.1; 536/23.1, 24.32

[56] References Cited

U.S. PATENT DOCUMENTS 5,262,156  11/1993  Alemohammed ..................... 424/92

OTHER PUBLICATIONS

Sharma et al. "Characterization of gastric epithelial cell . . . " *Amer. J. Gastroenterol.* 89(8), Abstract 244, p. 1346, 1994.
Noach et al. "Mucosal Tumor Necrosis Factor–alpha . . . " *Scand. J. Gastroenterol.* 425–429, 1994.
Peek et al. "cagA–positive *Helicobacter pylori* strains . . . ", Abstract 209, p. A–53, American Gasteroenterol. Assoc. Meeting, New Orleans, LA, 1994.
Tummuru et al. "Cloning and Expression of a High–Molecular–Mass . . . ", *Infect. and Immun.* 61(5):1799–1809, May 1993.
Blaser, M. J. "Hypothesis on the pathogenesis and natural history of . . . " *Gastroenterol.* 102:720–727, 1992.
Talley et al. "Gastric Adenocarcinoma and *Helicobacter pylori* Infection", *J. Nat. Cancer Inst.* 83:1734–1739, 1991.
Nomura et al. "*helicobacter pylori* infection and gastric carcinoma . . . Hawaii", *N. Engl. J. Med.* 325:1132–1136, 1991.
Peterson, W. L. "*Helicobacter pylori* and peptic ulcer disease", *N. Engl. J. Med.* 324:1043–1048, 1991.
Parsonnet et al. "*Helicobacter pylori* infection in intestinal– and diffuse–type–. . . ", *J. Nat. Cancer Inst.* 83:640–643, 1991.
Blaser, M. J. "*Helicobacter pylori* and the Pathogenesis of Gastroduodenal Inflammation", *J. Infect. Dis.* 161:626–633, 1990.

Primary Examiner—W. Gary Jones
Assistant Examiner—Dianne Rees
Attorney, Agent, or Firm—Needle & Rosenberg

[57] ABSTRACT

A cagB gene of *H. pylori* is provided. This nucleic acid can be the nucleic acid consisting of nucleotides 193 through 1158 in the sequence set forth as SEQ ID NO:1, which is an example of a native coding sequence for CagB. This nucleic acid can also be in a vector suitable for expressing a polypeptide encoded by the nucleic acid. A cagC gene of *H. pylori* is provided. This nucleic acid can be the isolated nucleic acid consisting of nucleotides 1170 through 3830 in the sequence set forth as SEQ ID NO:3, which is an example of a native coding sequence for CagC. This nucleic acid can also be in a vector suitable for expressing a polypeptide encoded by the nucleic acid. Isolated nucleic acids that specifically hybridize with cagB and cagC are provided. CagB and CagC are associated with peptic ulceration and other clinical syndromes in humans infected with strains of *H. pylori* that express it.

14 Claims, 2 Drawing Sheets

CAGB AND CAGC GENES OF HELICOBACTER PYLORI AND RELATED COMPOSITIONS

This invention was made with government support under Grant No. ROICA 58834, awarded by the National Institutes of Health. The Government has certain rights in the invention.

BACKGROUND OF THE INVENTION

1. Statement of the Invention

The invention pertains to the cagB and the cagC genes of *Helicobacter pylori* and to the antigenic polypeptides encoded by the genes, as well as methods of using the genes and polypeptides to diagnose *H. pylori* infection and predisposition to peptic ulceration and other diseases associated with *H. pylori* infection.

2. Background Art

*Helicobacter pylori* was first isolated in 1983 from gastric biopsy specimens of patients with chronic gastritis (1). A wide body of evidence, from studies that include human volunteer challenges, animal models and treatment with antimicrobial agents, indicates that *H. pylori* plays a critical and necessary role in the pathogenesis of chronic superficial gastritis (2). This condition remains asymptomatic in most infected persons but considerably increases the risk of peptic ulcer (3,4) and gastric adenocarcinoma (5–8). Treatment of patients with peptic ulcers with antibiotics to eradicate *H. pylori* infection results in ulcer healing and markedly reduced ulcer recurrence rates (9).

Pathogenic mechanisms of *H. pylori* are poorly understood, but the existence of ulcerogenic strains of this bacterium may explain why only a minority of patients harboring the organism develop duodenal ulcer disease. Two virulence factors produced by 50–60% *H. pylori* of strains are (A) a secreted cytotoxin that induces vacuolation in eukaryotic cells (10,11) and (B) a high molecular weight (120–140 kDa) superficial protein the CagA antigen (12–16). From 88–100% of *H. pylori* strains that have been isolated from patients with duodenal ulceration possess CagA antigen whereas in patients with superficial gastritis alone, the prevalence is 50–60%. Recent in vivo studies using gastric biopsies from patients infected with *H. pylori* have shown that CagA+ strains induce significantly greater interleukin-1 alpha, interleukin-1 beta and interleukin-8 production than CagA negative strains (17). Further, in vitro studies have also shown that CagA+ strains induce greater levels of proinflammatory cytokines (interleukin-8) by gastric epithelial cells than CagA− strains (18).

However isogenic cagA− mutants induce similar cytokine levels as do the wild-type strains, indicating that whereas CagA is a marker for increased inflammation, its presence is not necessary (27). Because so little is known about the pathogenesis of *H. pylori*, there is a need to identify other genes present exclusively in wild type cagA+ strains.

The invention identifies two genes (cagB and cagC) that are present exclusively in CagA positive *H. pylori* strains and can encode 36 and 101 kDa proteins. The present data show that these genes are highly associated with duodenal ulcers, and that mutants deficient in these genes do not stimulate epithelial cells to produce the pro-inflammatory cytokine IL-8.

SUMMARY OF THE INVENTION

The invention pertains to the cagB gene of *H. pylori*. Thus, the invention provides an isolated nucleic acid encoding a polypeptide consisting of amino acids 1 through 322 in the sequence set forth as SEQ ID NO:1. This nucleic acid can be the nucleic acid consisting of nucleotides 193 through 1158 in the sequence set forth as SEQ ID NO:1, which is an example of a native coding sequence for CagB.

The invention pertains to the cagC gene of *H. pylori*. Thus, the invention provides an isolated nucleic acid encoding a polypeptide consisting of amino acids 1 through 887 in the sequence set forth in SEQ ID NO:3. This nucleic acid can be the isolated nucleic acid consisting of nucleotides 1170 through 3830 in the sequence set forth as SEQ ID NO:3, which is an example of a native coding sequence for CagC.

An isolated nucleic acid that specifically hybridizes with the nucleic acid consisting of nucleotides 193 through 1158 in the sequence set forth as SEQ ID NO:1, under polymerase chain reaction conditions is provided. The invention provides an isolated nucleic acid that specifically hybridizes with the nucleic acid consisting of nucleotides 193 through 1158 in the sequence set forth as SEQ ID NO:1 under the conditions of Tummuru et al. 1993 (15). An isolated nucleic acid that specifically hybridizes with the nucleic acid consisting of nucleotides 1170 through 3830 in the sequence set forth as SEQ ID NO:3, under polymerase chain reaction conditions is provided. The invention provides an isolated nucleic acid that specifically hybridizes with the nucleic acid consisting of nucleotides 1170 through 3830 in the sequence set forth as SEQ ID NO:3 under the above conditions.

A purified CagB protein is provided. As described below, CagB is associated with peptic ulceration and other clinical syndromes in humans infected with strains of *H. pylori* that express it. A purified CagC protein is provided. As described below, CagC is associated with peptic ulceration and other clinical syndromes in humans infected with strains of *H. pylori* that express it.

The present invention provides a method of detecting the presence of a *H. pylori* strain expressing the CagB antigen or the CagC antigen in a subject, comprising the steps of contacting an antibody-containing sample from the subject with a detectable amount of CagB or CagC or specific antigenic fragments, followed detecting the binding reaction of the CagB or CagC or fragment and the antibody produced by the subject. The binding indicating the presence of a toxic CagB- or CagC-expressing *H. pylori* strain or previous infection with a cytotoxic *H. pylori* strain. Also provided is a method of detecting *Helicobacter pylori* infection in a subject, comprising detecting the presence of a nucleic acid encoding CagB or CagC in a specimen from the subject, the presence of the nucleic acid indicating infection with *Helicobacter pylori*.

DETAILED DESCRIPTION OF THE INVENTION

Nucleic Acids cagB and cagC Genes

Figure 1:
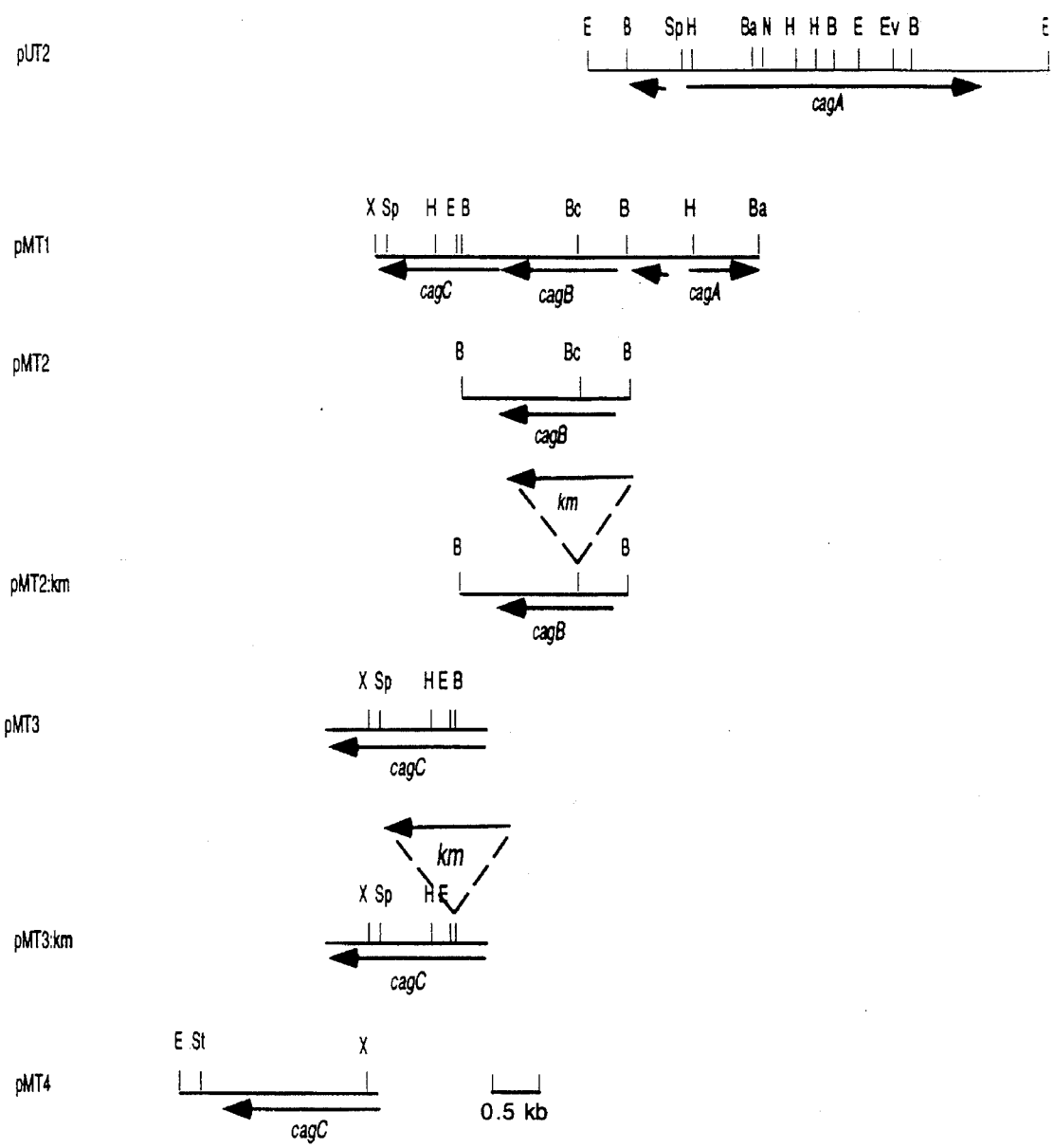
FIG. 1 shows the structure of cagA-, cagB-, and cagC-containing plasmids. Plasmid pUT2 contains cagA plus 1.0 kb upstream region. Plasmid pMT1 contains a 4.5 kb BamHI-XhoI fragment which hybridized to the cagA upstream probe. Arrows beneath the plasmids represent the location of the genes and direction of transcription. km represents kanamycin cassette from pILL600. Restriction endonuclease cleavage sites; B (BglII), Ba (BamHI), Bc (BclI), E (EcoRI), Ev (EcoRV), H (HindIII), N (NdeI), Sp (SspI), St (StuI), and X (XhoI).

The invention pertains to the cagB gene of *H. pylori*. Thus, the invention provides an isolated nucleic acid encoding a polypeptide consisting of amino acids 1 through 322 in the sequence set forth as SEQ ID NO:1. This nucleic acid can be the nucleic acid consisting of nucleotides 193 through 1158 in the sequence set forth as SEQ ID NO:1, which is an example of a native coding sequence for CagB.

The invention pertains to the cagC gene of *H. pylori*. Thus, the invention provides an isolated nucleic acid encoding a polypeptide consisting of amino acids 1 through 887 in the sequence set forth in SEQ ID NO:3. This nucleic acid can be the isolated nucleic acid consisting of nucleotides 1170 through 3830 in the sequence set forth as SEQ ID NO:3, which is an example of a native coding sequence for CagC.

Although the cagB and cagC genes for specific *H. pylori* strains are exemplified, it is recognized that other *H. pylori* strains have cagB and cagC genes that are homologs of the exemplary nucleic acids that encode homologs of CagB and CagC. Having provided examples of the cagB and cagC genes, homologs can be routinely recognized in other CagB and CagC expressing strains by sequence comparison to the exemplary sequences to determine the degree of sequence similarity. The homologs can be obtained, for example, by using the exemplary nucleic acids or unique fragments thereof as probes or primers in routine methods such as the Southern hybridization or polymerase chain reaction (PCR) methods taught in the examples.

Because cagB and cagC are demonstrated by Northern blot to be transcribed together as a single transcript, they appear to exist in an operon. Additionally, as described below cagA is closely linked to cagB and cagC, such that strains that are cagA$^+$ are typically also positive for cagB and cagC. However, there could exist strains that are cagA$^+$, but cagB and cagC negative.

Having identified an operon for cagB and cagC, the regulatory sequences for these genes can be routinely identified. For example the present invention discloses a putative promoter sequence for cagB and a stem-loop structure for CagC. Additionally, using reporter genes such as a promoterless cat (choramphenicol acetyl transferase) introduced via mini Tn3 km-cat construct, as described in Ferrero et al. (24), other regulatory sequences of cagB and cagC can be characterized. Thus, the regulatory sequences could be used to screen for compounds that inhibit or enhance transcription of the genes. For example, antisense nucleotides can be designed which bind to the regulatory regions and inhibit the expression of the genes.

SEQ ID Nos:1–4 show the nucleotide and amino acid sequences of the cagB and cagC genes. The nucleotide sequence of the 3989 bp fragment is depicted, with the deduced CagB and CagC proteins translated. Predicted promoter elements (–35 and –10 sequences, nucleotides 77–80 and 97–102, respectively) and potential ribosome binding sites (nucleotides 183–187 and 1163–1167) are identified. There is a proposed cleavage site between amino acids 22 and 23 of the predicted leader peptide by signal peptidaseI. A consensus ATP/GTP binding site (a.a. 597–605) is identified. Also identified is a region of dyad symmetry (nucleotides 3844–3874) which could function as a transcription termination structure (G=–6.3) immediately downstream of the cagC ORF.

Specifically Hybridizing Nucleic Acids

An isolated nucleic acid that specifically hybridizes with the nucleic acid consisting of nucleotides 193 through 1158 in the sequence set forth as SEQ ID NO:1, under polymerase chain reaction conditions is provided. For example, the hybridizing nucleic acid can be primer consisting of a unique fragment of the reference sequence that hybridizes only to the exemplified cagB gene or a *H. pylori* homolog thereof.

The invention provides an isolated nucleic acid that specifically hybridizes with the nucleic acid consisting of nucleotides 193 through 1158 in the sequence set forth as SEQ ID NO:1 under the conditions of 68° C. for 16 hours in buffer containing 6 X SSC, 0.5% sodium dodecyl sulfate, 5 X Denhardt's solution and 100 µg salmon sperm DNA, with washing at 60° C. in 0.5 X SSC (15). For example, the hybridizing nucleic acid can be a probe that hybridizes only to the exemplified cagB gene or a homolog thereof. The hybridizing nucleic acid can also be a homolog of the exemplified cagB gene that hybridizes only to the exemplified cagB gene or other *H. pylori* homologs of the exemplified cagB gene.

An isolated nucleic acid that specifically hybridizes with the nucleic acid consisting of nucleotides 1170 through 3830 in the sequence set forth as SEQ ID NO:3, under polymerase chain reaction conditions is provided. For example, the hybridizing nucleic acid can be primer consisting of a unique fragment of the reference sequence that hybridizes only to the exemplified cagC gene or a *H. pylori* homolog thereof.

The invention provides an isolated nucleic acid that specifically hybridizes with the nucleic acid consisting of nucleotides 1170 through 3830 in the sequence set forth as SEQ ID NO:3 under the conditions of 68° C. for 16 hours in buffer containing 6 X SSC, 0.5% sodium dodecyl sulfate, 5 X Denhardt's solution and 100 µg salmon sperm DNA, with washing at 60° C. in 0.5 X SSC.(15). For example, the hybridizing nucleic acid can be a probe that hybridizes only to the exemplified cagC gene or a homolog thereof. The hybridizing nucleic acid can also be a homolog of the exemplified cagC gene that hybridizes only to the exemplified cagC gene or other *H. pylori* homologs of the exemplified cagC gene.

The exemplary sequences for cagB and cagC are understood to be double stranded. The double stranded nucleic acids of the invention can be denatured so that each individual strand of the nucleic acid is exposed. In this manner the hybridizing nucleic acids can hybridize with either strand of the exemplary nucleic acids or their *H. pylori* homologs.

The specifically hybridizing nucleic acids can comprise fragments of the specific genes that are unique based on a comparison with other nucleotide sequences in the available databases (e.g., GenBank). Comparisons of this type are routinely practiced in the art. In this manner regions of the present genes that are not identical to other genes can be identified. In comparisons with other sequences submitted to GenBank, no significant cagB homologs or significantly similar sequences were found. Similarly, in comparisons with other sequences submitted to GenBank, no significant cagC homologs or significantly similar sequences were found. Unique fragments of the present genes could be useful as primers for specific amplification of the genes (and homologs) or as coding sequences for antigenic fragments of CagB and CagC.

CagB and CagC Polypeptides

A purified CagB protein is provided. As described below, CagB is associated with peptic ulceration and other clinical syndromes in humans infected with strains of *H. pylori* that express it. An example of this protein is a polypeptide consisting of amino acids 1 through 322 in the sequence set forth as SEQ ID NO:1. This is the deduced amino acid sequence of an approximately 36 kDa CagB protein produced by strain 84–183 of *H. pylori* (ATCC53726), which is naturally encoded in this strain by the nucleic acid consisting of nucleotides 193 through 1158 in the sequence set forth as SEQ ID NO:1.

Having provided an example of a purified CagB protein, the invention also enables the purification of CagB homologs from other *H. pylori* strains that express CagB. For example, an antibody raised against the exemplary protein can be used routinely to screen preparations of other *H. pylori* strains for homologous proteins that react with the CagB-specific antibody.

Also within the scope of the invention is a purified antigenic polypeptide encoded by a nucleic acid that specifically hybridizes with the nucleic acid consisting of nucleotides 193 through 1158 in the sequence set forth as SEQ ID NO:1 under the conditions given in Tummuru et al. 1993 (15). The antigenic polypeptide can be an antigenic fragment of the exemplary CagB protein. The antigenic polypeptide can be a homolog of the exemplified CagB protein or a fragment of a homolog.

A purified CagC protein is provided. As described below, CagC is associated with peptic ulceration and other clinical syndromes in humans infected with strains of *H. pylori* that express it. An example of this protein is a polypeptide consisting of amino acids 1 through 887 in the sequence set forth in SEQ ID NO:3. This is the deduced amino acid sequence of an approximately 101 kDa CagC protein produced by strain 84–183 of *H. pylori* (ATCC53726), which is naturally encoded in this strain by the nucleic acid consisting of nucleotides 1170 through 3830 in the sequence set forth as SEQ ID NO:3.

Having provided an example of a purified CagC protein, the invention also enables the purification of CagC homologs from other *H. pylori* strains that express CagC. For example, an antibody raised against the exemplary protein can be used routinely to screen preparations of other *H. pylori* strains for homologous proteins that react with the CagC-specific antibody.

Also within the scope of the invention is a purified antigenic polypeptide encoded by a nucleic acid that specifically hybridizes with the nucleic acid consisting of nucleotides 1170 through 3830 in the sequence set forth as SEQ ID NO:3 under the conditions given in Tummuru et al. 1993 (15). The antigenic polypeptide can be an antigenic fragment of the exemplary CagC protein. The antigenic polypeptide can be a homolog of the exemplified CagC protein or a fragment of a homolog.

Since the invention provides the sequences of novel *H. pylori* genes and the deduced amino acid sequences of the respective proteins, the amino acid sequences can be analyzed to identify domains of the protein essential either for natural function or antigenicity. For example, in the same manner used in Example 1 to identify a perfect ATP/GTP binding site in CagC, other key functional regions of the proteins are identified. Such core sequences can be used, for example, as a reagent in an immunoassay to detect infection with particular strains of *H. pylori*.

Antigenic Fragments

An antigenic fragment of the antigen can be selected by applying the routine technique of epitope mapping to the CagB or CagC proteins to determine the regions of the proteins that contain epitopes reactive with serum antibodies or are capable of eliciting an immune response in an animal. Once the epitope is selected, an antigenic polypeptide containing the epitope can be synthesized directly, or produced recombinantly by cloning nucleic acids encoding the polypeptide in an expression system, according to the standard methods. Alternatively, an antigenic fragment of the antigen can be isolated from the whole antigen or a larger fragment by chemical or mechanical disruption. The purified fragments thus obtained can be tested to determine their antigenicity and specificity by the methods taught herein. An antigenic fragment is defined as an amino acid sequence of at least about 5 consecutive amino acids derived from the antigen amino acid sequence that is reactive with (binds) an antibody.

Additionally, methods are known for comparing CagB or CagC with other known proteins to select regions of the protein that are unique to CagB or CagC. An example of such a comparison is described in Example 1, which compares the deduced amino acid sequence of CagC to the *Bordatella pertussis* toxin secretion protein. The same well known methods can be used to compare the present proteins to other proteins submitted to the public databases. Thus, any unique polypeptides of the present proteins can be routinely identified. The unique fragments can be tested for antigenicity and specificity as taught herein.

Once the amino acid sequence of the antigenic polypeptide is provided, antigenic polypeptides can be designed that correspond to amino acid sequences of the native antigen, but with modifications in the form of substitutions, inclusions or deletions of particular amino acid residues in the derived sequences. The modifications can include attaching the antigen to sequences designed to provide for some additional property, such as solubility. The modifications can include other amino acids that provide for some additional property, such as to remove/add amino acids capable of disulfide bonding, to increase bio-longevity, alter enzymatic activity, or alter interactions with gastric acidity. In any case, the peptide must possess a bioactive property, such as antigenicity, immunogenicity, specificity etc. The polypeptides so designed can be tested for antigenicity, immunogenicity and specificity by the methods used and described herein. These polypeptides can then be synthesized, using standard peptide synthesis techniques. Thus, synthesis or purification of an extremely large number of functional polypeptides derived from the exemplary sequence of the present antigens is possible.

Determining Immunogenicity

The purified antigenic polypeptides can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the bacterium to determine the vaccine effect of the specific antigenic fragment. The specificity of the fragment can be ascertained by testing sera, other fluids or lymphocytes from the inoculated animal for cross reactivity with other closely related bacteria.

Vectors and Hosts

A vector comprising the nucleic acids of the present invention is also provided. The nucleic acid can encode a functional CagB or CagC protein or a fragment thereof. By "functional" is meant a polypeptide that possesses the native function of the protein or a polypeptide that possesses antigenicity. The vector can include regulatory sequences from the native *H. pylori* cagB or cagC genes as well as other *H. pylori* DNA so long as the expression of functional CagB or CagC or fragments thereof is not prevented. The vector of the invention can be in a host suitable for expressing the polypeptide encoded by the nucleic acid.

For example the individual coding sequences are subcloned for the separate expression of the CagB and CagC proteins. Additionally, a vector can contain the whole genomic region with both cagB and cagC. Examples of such vectors are provided in the examples.

There are numerous *E. coli* expression vectors known to one of ordinary skill in the art useful for the expression of the antigen. Other microbial hosts suitable for use include bacilli, such as Bacillus subtilus, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Antigen Bound to Substrate

A purified CagB antigen bound to a substrate is provided. A purified CagC antigen bound to a substrate is also provided. The antigen can also be bound to a purified antibody or ligand. The antibody can be a monoclonal antibody obtained by standard methods and as described herein.

Mutant H. pylori

A mutant *Helicobacter pylori* in which the product of the cagB gene is nonfunctional is provided. The mutant can either not express CagB or express a non-functioning CagB antigen. In one example, the mutant *H. pylori* strain is obtained by making an insertional mutation in the coding sequence for the CagB antigen as described in Example 2. For example the mutant can be one in which the nucleic acid consisting of nucleotides 193 through 1158 in the sequence set forth as SEQ ID NO:1 has been rendered nonfunctional. The mutant *Helicobacter pylori* can be the *Helicobacter pylori* deposited with the American Type Culture Collection, 12301 Parklawn Drive, Rockville, Md. 20852, under ATCC Accession Number 55611. Because other strains expressing CagB can now be identified based on the disclosure of the cagB gene, the cagB genes of other *H. pylori* strains can be mutagenized to produce a mutant of the invention. Since the present invention provides the nucleic acid encoding the antigen, other methods of mutating the coding sequence of the antigen can be used to obtain other mutant strains as contemplated herein.

A mutant *Helicobacter pylori* in which the product of the cagC gene is nonfunctional is provided. The mutant can either not express CagC or express a non-functioning CagC antigen. In one example, the mutant *H. pylori* strain is obtained by making a substitution mutation in the coding sequence for the CagC antigen as described in Example 2. For example the mutant can be one in which the nucleic acid consisting of nucleotides 1170 through 3830 in the sequence set forth as SEQ ID NO:3 has been rendered nonfunctional. The mutant *Helicobacter pylori* can be the *Helicobacter pylori* deposited with the American Type Culture Collection under ATCC Accession Number 55612. Because other strains expressing CagC can now be identified based on the disclosure of the cagC gene, the cagC genes of other *H. pylori* strains can be mutagenized to produce a mutant organism of the invention. Since the present invention provides the nucleic acid encoding the CagC antigen, other methods of mutating the coding sequence of the antigen can be used to obtain other mutant strains as contemplated herein.

Additional isogenic mutants can be prepared, for example, by inserting a nucleic acid in the cagB or cagC genes or deleting a portion of the cagB or cagC genes so as to render the gene non-functional or produced in such low amounts that the organism is non-infectious. Furthermore, by providing the nucleotide sequence for the nucleic acid encoding the antigen, the present invention permits the making of specific point mutations having the desired effect. The deletion, insertion or substitution mutations can be made in the gene sequence in either the regulatory or coding region to prevent transcription or to render the transcribed product nonfunctional.

One such approach to the construction of a deletion or insertion mutant is via the Donnenberg method (33). A deletion in cagB is created by deleting a 0.2 kb PvuI-Bcl I fragment and religating the cagB clone. This mutant is cloned into suicide vector pILL570. The sacB gene of *Bacillus subtilis* can also be cloned into the suicide vector to provide a conditionally lethal phenotype. This construct can be transformed into *H. pylori* by electroporation, and transformants selected by spectinomycin resistance. The merodiploid strain which contains the suicide vector and the mutated version of the cagB gene are exposed to sucrose to directly select for organisms that have undergone a second recombination, resulting in the loss of the vector. These and other well known methods of making mutations can be applied to the nucleic acids provided herein to obtain other desired mutations. Parallel methods can be used to produce cagC mutants.

Non-isogenic mutants are also within the scope of the invention. For example, a live attenuated *H. pylori* that is also a cagB and cagC$^-$ mutant according to the present invention, is provided. A cagB$^-$recA$^-$ mutant strain or cagC$^-$recA$^-$ strain is constructed, for example, by insertion mutation of the cagB or cagC and recA genes, according to the methods taught herein and taught in U.S. Ser. No. 08/215,928 for recA. A cagB$^-$vacA$^-$ mutant strain or a cagC$^-$vacA$^-$ mutant strain is constructed, for example, by insertion mutation of the cagB or cagC and vacA genes, according to the methods taught herein for cagB and cagC and in U.S. application Ser. No. 08/215,928, which describes the generation of a vacA mutant. A recA$^-$cagB$^-$vacA$^-$ mutant strain or a recA$^-$cagC$^-$vacA$^-$ mutant strain is constructed, for example, by insertion mutation of the recA, cagB or cagC and vacA genes, according to the methods taught herein for cagB and cagC, and taught in U.S. Ser. No. 08/215,928 for recA and vacA. Mutant strains that are also cagA$^-$ can be made by the methods disclosed herein. Any of the well known methods of mutating a gene can be used in the present invention to generate *H. pylori* mutant strains. The strains can be tested as provided for immunogenicity.

Purified Antibodies

A purified monoclonal antibody that specifically binds the CagB antigen or antigenic fragment is also provided. A purified monoclonal antibody that specifically binds the CagC antigen or antigenic fragment is also provided. The antibody can specifically bind a unique epitope of the antigen it can also bind epitopes of other organisms. The term "bind" means the well understood antigen/antibody binding as well as other nonrandom association with an antigen. "Specifically bind" as used herein describes an antibody or other ligand that does not cross react substantially with any antigen other than the one specified, in this case, the CagB antigen or the CagC antigen. Antibodies can be made as described in Harlow and Lane (34)). Briefly, purified antigen can be injected into an animal in an amount and in intervals sufficient to elicit an immune response. Polyclonal antibodies can be purified directly, or spleen cells from the animal can be fused with an immortal cell line and screened for monoclonal antibody secretion. Thus, nonhuman polyclonal antibodies that specifically bind the antigen are within the scope of the present invention.

A ligand that specifically binds the antigen is also contemplated. The ligand can be a fragment of an antibody or a smaller molecule designed to bind an epitope of the antigen. The antibody or ligand can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Serological Detection (Diagnosis) Methods
Detecting Antibody with Antigen

The present invention provides a method of detecting the presence of a *H. pylori* strain expressing the CagB antigen or the CagC antigen in a subject, comprising the steps of contacting an antibody-containing sample from the subject with a detectable amount of CagB or CagC or specific antigenic fragments, followed detecting the binding reaction of the CagB or CagC or fragment and the antibody produced by the subject. The binding indicating the presence of a toxic CagB- or CagC-expressing *H. pylori* strain or previous infection with a toxic *H. pylori* strain. There are numerous routine immunological assays that can be used in the present detection and predisposition methods. Examples are provided below.

ELISA

Immunoassays such as immunofluorescence assays (IFA), enzyme linked immunosorbent assays (ELISA) and immunoblotting can be readily adapted to accomplish the detection of the antibody. An ELISA method effective for the detection of the antibody can, for example, be as follows: (1) bind the antigen to a substrate (e.g., an ELISA plate); (2) contact the bound antigen with a fluid or tissue sample containing the antibody; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antigen as well as antibody.

Detecting Antigen with Antibody/Ligand

One example of the method of detecting *H. pylori* possessing the antigen is performed by contacting a fluid or tissue sample from the subject with an amount of a purified antibody specifically reactive with the antigen, and detecting the binding of the antibody with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.

Competitive Inhibition Assay

Another immunologic technique that can be useful in the detection of *H. pylori* expressing CagB or CagC or previous *H. pylori* infection utilizes monoclonal antibodies (MAbs) for detection of antibodies specifically reactive with antigen. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of the CagB/CagC-possessing *H. pylori* strain in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides a CagB antigen and a CagC antigen for the detection of toxic *H. pylori* or previous *H. pylori* infection other serological methods such as flow cytometry and immunoprecipitation can also be used as detection methods.

In the diagnostic methods taught herein, the antigen can be bound to a substrate and contacted by a fluid sample such as serum, urine, saliva or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or non-specifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy), alkaline phosphatase (for biochemical detection by color change) and radioisotopes (for radiography). The detection methods and moieties used can be selected, for example, from the list above or other suitable examples by the standard criteria applied to such selections ( 34 ).

Vaccines

The CagB or CagC antigens, antigenic fragments or mutant *H. pylori* of this invention can be used in the construction of a vaccine. Thus, the invention provides an immunogenic amount of the CagB or CagC antigen or mutant *H. pylori* in a pharmaceutically acceptable carrier. The vaccine can be the entire antigen, the antigen on an intact *H. pylori, E. coli* or other strain. The vaccine can then be used in a method of preventing peptic ulceration or other complications of *H. pylori* infection (including atrophic gastritis and malignant neoplasms of the stomach).

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier in the vaccine of the instant invention can comprise saline or other suitable carriers (35). An adjuvant can also be a part of the carrier of the vaccine, in which case it can be selected by standard criteria based on the antigen used, the mode of administration and the subject (35). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating *H. pylori* infection and the associated diseases by administering the vaccine to a subject.

Detecting Disease or Predisposition to Disease

Peptic Ulceration

Because the purified CagB and CagC antigens provided herein are associated with peptic ulceration, the present invention also provides a method of determining predisposition to peptic ulceration in a subject. The method can be accomplished according to the methods set forth herein for the detection of *H. pylori* expressing the CagB and CagC antigens or for the detection of antibodies specific to the antigens. The presence of the antigen or specific antibodies indicates a predisposition of the subject to peptic ulceration. The methods described below for detecting nucleic acids specific for $cagB^+cagC^+$ strains can also be used.

Gastric Carcinoma

Because the purified CagB and CagC proteins of *H. pylori* provided herein are essential for IL-8 elaboration in gastric cells, they are likely associated with gastric cancer. Thus, the present invention also provides a method of determining predisposition to gastric carcinoma in a subject. The method can be accomplished according to the methods set forth herein for the detection of $cagB^+$ or $cagC^+$ *H. pylori* strains or for the detection of antibodies specific to the CagB or CagC antigens. The presence of the antigens or specific antibodies indicates a predisposition of the subject to gastric carcinoma. The methods described herein for detecting nucleic acids specific for $cagB^+$ or $cagC^+$ strains can also be used.

Treatment Methods

Methods of treating peptic ulcers in a subject using the compositions of the present invention are provided. For example, in one such method an amount of ligand (e.g., antibody or antibody fragment) specifically reactive with the CagB or CagC antigen of *H. pylori* sufficient to bind the antigen in the subject and improve the subject's clinical condition is administered to the subject. Such improvement results from the ligand interfering with the antigen's normal function in inducing inflammation and cellular damage. The ligand can be a purified monoclonal antibody specifically reactive with the antigen, a purified polyclonal antibody derived from a nonhuman animal, or other reagent having specific reactivity with the antigen. Additionally, cytotoxic moieties can be conjugated to the ligand/antibody by standard methods. Examples of cytotoxic moieties include ricin A chain, diphtheria toxin and radioactive isotopes.

Another method of treating peptic ulcers in a subject comprises administering to the subject an amount of a ligand/antagonist for a receptor for the CagB or CagC antigens of *H. pylori* sufficient to react with the receptor and prevent the binding of the CagB or CagC antigens to the receptor. An antagonist for the receptor is thus contemplated. The result is an improvement in the subject's clinical condition. Alternatively, the treatment method can include administering to the subject an amount of an analogue of a receptor for the antigen to result in competitive binding of the antigen, thus inhibiting binding of the antigen to its wild type receptor. The receptor is localized on cells present in the gastroduodenal mucosa, such as epithelial cells, inflammatory cells, or endothelial cells.

It is also contemplated that CagB or CagC could be used to stimulate IL-8 production in a subject, because both proteins are associated with the elaboration of IL-8 in gastric cells. Therefore, any treatment calling for production or enhanced production of IL-8 can use the present proteins. If a genetic condition prevents sufficient IL-8 elaboration, the present cagB or cagC genes can be administered to a subject to provide IL-8 production.

Because the expression of CagB and CagC is shown to be associated with gastric carcinoma, the above treatment methods are applicable to the treatment or prevention of gastric carcinoma.

The following examples are intended to illustrate, but not limit, the invention. While they are typical of those that might be used, other procedures known to those skilled in the art may be alternatively employed.

Nucleic Acid Diagnostic Methods

A method of detecting *Helicobacter pylori* infection in a subject, comprising detecting the presence of a nucleic acid encoding CagB in a specimen from the subject, the presence of the nucleic acid indicating infection with *Helicobacter pylori*. More particularly, the detection of a nucleic acid encoding CagB indicates the presence of a strain of *H. pylori* that expresses CagB. In an example of the method, the nucleic acid detected is the nucleic acid consisting of nucleotides 193 through 1158 in the sequence set forth as SEQ ID NO:1. This nucleic acid is one example of a cagB gene identified in a particular $cagB^+$ strain. It is understood that other strains that are $cagB^+$ can be detected by detecting the presence of homologs of the exemplary cagB gene using routine methods, such as hybridization with the specifically hybridizing nucleic acids of the invention.

A method of detecting *Helicobacter pylori* infection in a subject, comprising detecting the presence of a nucleic acid encoding CagC in a specimen from the subject, the presence of the nucleic acid indicating infection with *Helicobacter pylori*. More particularly, the detection of a nucleic acid encoding CagC indicates the presence of a strain of *H. pylori* that expresses CagC. In an example of the method, the nucleic acid detected is the nucleic acid consisting of nucleotides 1170 through 3830 in the sequence set forth as SEQ ID NO:3. This nucleic acid is one example of a cagC gene identified in a particular cagC$^+$ strain. It is understood that other strains that are cagC$^+$ can be detected by detecting the presence of homologs of the exemplary cagC gene using routine methods, such as hybridization with the specifically hybridizing nucleic acids of the invention.

Unique fragments of the cagB or cagC genes can be detected in a sample to diagnose *H. pylori* infection in a subject. The specificity of these sequences for their respective antigens can be determined by conducting a computerized comparison with known sequences, catalogued in GenBank, a computerized database, using the available computer programs, such as Word Search or FASTA of the Genetics Computer Group (Madison, Wis.), which search the catalogued nucleotide sequences for similarities to the gene or fragment in question. An example of the use of a comparison program for the determination of uniqueness of a nucleic acid is given in the Examples. Using these routine methods, probes and primers can be designed that specifically hybridize with or amplify some unique portion of the cagB or CagC genes, so that amplification or hybridization provides a reliable diagnosis of *H. pylori* infection.

The nucleic acid specific for the antigen can be detected utilizing a nucleic acid amplification technique, such as polymerase chain reaction or ligase chain reaction. Alternatively, the nucleic acid is detected utilizing direct hybridization or by utilizing a restriction fragment length polymorphism. For example, the present invention provides a method of detecting the presence of *H. pylori*, possessing the CagB or CagC antigen, comprising ascertaining the presence of a nucleotide sequence associated with a restriction endonuclease cleavage site. In addition, PCR primers which hybridize only with nucleic acids specific for the antigen can be utilized. The presence of amplification indicates the presence of the antigen. In another embodiment a restriction fragment of a DNA sample can be sequenced directly using, for example, Sanger ddNTp sequencing or 7-deaza-2'-deoxyguanosine 5'-triphosphate and Taq polymerase and compared to the known unique sequence to detect *H. pylori*. In yet another embodiment *H. pylori* can be detected by directly hybridizing the unique sequence with a cagB-specific or a cagC-specific nucleic acid probe. Furthermore, the nucleic acids in a sample can be amplified prior to hybridization by the methods described herein.

Detection of cagB or cagC in a sample using direct probing involves the use of oligonucleotide probes which may be prepared, for example, by restriction enzyme digestion of a nucleic acid, by synthesis or by nick translation. The probes may be suitably labeled using, for example, a radio label, enzyme label, fluorescent label, biotin-avidin label and the like for subsequent visualization, for example, in a Southern blot hybridization procedure. The labeled probe is reacted with a bound sample DNA, e.g., to a nitrocellulose sheet under conditions such that only complementary sequences or specifically hybridizing sequences will hybridize. The nucleic acids that hybridize to the labeled DNA probe become labeled themselves as a consequence of the reannealing reaction. The areas of the filter that exhibit such labeling may then be visualized, for example, by autoradiography. Hybridization conditions and visualization are exemplified in the Examples.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence of a mutation, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced. Following PCR, direct visualization or allele-specific oligonucleotide hybridization may be used to detect disease associated with a gene product.

In general, primers for PCR and LCR are usually about 20 bp in length and the preferable range is from 15–25 bp. Better amplification is obtained when both primers are the same length and with roughly the same nucleotide composition. PCR conditions can include denaturation of strands, usually takes place at 94° C., and extension from the primers is usually at 72° C. The annealing temperature varies according to the sequence under investigation. Examples of reaction times are: 20 mins denaturing; 35 cycles of 2 min, 1 min and 1 min for denaturation, annealing and extension, respectively; and finally a 5 min extension step. The skilled artisan is well aware of the numerous routine adjustments that can be made to the each of the PCR parameters to optimize PCR for the detection of a given nucleic acid.

Once specific variable sequences or point mutations are shown to be associated with disease (peptic ulceration, gastric carcinoma, etc.), the methods to detect these sequences are standard in the art. Detection of point mutations or variable sequences using direct probing involves the use of oligonucleotide probes which may be prepared, for example, synthetically or by nick translation. The probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. For the detection of specific point mutations or sequences that are conserved among the genes of the various strains, the labeled probe is reacted with a DNA sample bound to, for example, nitrocellulose under conditions such that only fully complementary sequences will hybridize. The stringency of hybridization is usually 5° C. below the Ti (the irreversible melting temperature of the hybrid formed between the probe and its target sequence) for the given chain length. For 20mers the recommended hybridization temperature is about 58° C. The washing temperatures are unique to the sequence under investigation and need to be optimized for each variant.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on *H. pylori* isolates or samples obtained from an individual, it can serve as a method of detecting the presence of the mutations.

In yet another method, PCR may be followed by restriction endonuclease digestion with subsequent analysis of the resultant products. Nucleotide substitutions can result in the gain or loss of specific restriction endonuclease site. The gain or loss of a restriction endonuclease recognition site facilitates the detection of the disease associated mutation using restriction fragment length polymorphism (RFLP) analysis or by detection of the presence or absence of a polymorphic restriction endonuclease site in a PCR product that spans the sequence of interest.

For RFLP analysis, DNA is obtained, for example from the blood, gastric specimen, saliva, dental plaque, other bodily fluids or stool of the subject suspected of containing antigen-possessing *H. pylori*, or *H. pylori* isolated from subject, and from a subject infected with nontoxic *H. pylori*, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, cagB or cagC DNA is detected by determining the number of bands detected and comparing this number to the DNA from H. pylori strains that are not associated with severe disease. Restriction endonucleases can also be utilized effectively to detect mutations in the present genes.

Similar creation of additional restriction sites by nucleotide substitutions at the disclosed mutation sites can be readily calculated by reference to the genetic code and a list of nucleotide sequences recognized by restriction endonucleases. Alternatively, an adaptation of PCR called amplification of specific alleles (PASA) can be employed; this uses differential amplification for rapid and reliable distinction between alleles that differ at a single base pair. Other techniques, such as 3SR, which utilize RNA polymerase to achieve high copy number, can also be used where appropriate. Single strand conformational analysis (SSCA) offers a relatively quick method of detecting sequence changes which may be appropriate in at least some instances.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the same disease.

EXAMPLE 1

Molecular Characterization of Cytotoxin Associated CagB,C Operon in *Helicobacter pylori*.

Loss of the CagA protein does not have any effect on cytotoxin activity. cagB and cagC are associated with the production of CagA and cytotoxin. Delineation of the nucleotide sequence of a 4.0 kilobase pair upstream region of cagA allowed the identification of 966 bp (cagB) and 2661 bp (cagC) open reading frames encoding 322 (36 kDa) and 887 (101 kDa) residue polypeptides, respectively. A potential signal sequence which contained two possible cleavage sites was identified in CagB. cagB and cagC are arranged in an operon, in opposite orientation to cagA. The deduced cagC product showed a significant homology (26% identity and 50% similarity) with the *Bordetella pertussis* toxin secretion protein. In a study of 55 *H. pylori* strains isolated from patients with gastritis alone or with duodenal ulcers, the cagB and cagC genes were present in all strains that are isolated from patients with duodenal ulceration, whereas only 59% of strains from gastritis patients possess the cagB or cagC genes. These studies suggest an association of cagB and cagC genes with peptic ulceration.

Bacterial strains, plasmids, and growth conditions

*H. pylori* 84–183 (ATCC53726) was used to clone the cagB, C genes. Fifty-five clinical *H. pylori* isolates from patients with gastritis alone or with duodenal ulceration were used to determine the correlation between the presence of cagB,C genes in *H. pylori* and their association with gastritis or duodenal ulceration. Stock cultures were maintained at −70° C. in Brucella broth (BBL Microbiology Systems, Cockeysville, Md.) supplemented with 15% glycerol. *Escherichia coli* DH5-alpha and XL-1 Blue (Stratagene, LaJolla, Calif.) were used for transformation. Plasmid pBluescript (Stratagene) was used as a cloning vector. *E. coli* strains were routinely cultured in Luria Broth (LB) medium with shaking at 37° C., and *H. pylori* strains were cultured in Trypticase soy agar plates containing 5% sheep blood in a microaerobic atmosphere at 37° C. for 48 h.

Chemicals and enzymes

Isopropyl-B-D-thiogalactopyranoside (IPTG) was purchased from Sigma Chemical Co. (St. Louis, Mo.) and used at 50 µg/ml. Restriction enzymes, T4 DNA ligase, *E. coli* DNA polymerase large (Klenow) fragment, and Seguenase were obtained from GIBCO-BRL (Gaithersburg, Md.) and United States Biochemicals (Cleveland, Ohio). ($^{32}$P)dATP (650 Ci/mmol) was obtained from ICN Radiochemicals (Irvine, Calif.)

Genetic techniques and Nucleotide sequence analysis

Chromosomal DNA was prepared as described previously (15). Plasmids were isolated by the procedure of Birnboim and Doly (19). All other standard molecular genetic techniques were performed as described previously (20). The nucleotide sequence was determined unambiguously on both strands by using double-stranded DNA templates and the dideoxy chain termination procedure as described previously (21). Oligonucleotide primers were synthesized at the Vanderbilt University DNA core Facility with a Milligen 7500 DNA synthesizer. Nucleotide sequences were compiled and analyzed with the aid of the GCG program (Genetics Computer Group, Madison, Wisconsin).

Construction of a genomic library from *H. pylori*

Strain 84–183 chromosomal DNA was partially digested with Sau3A and the resulting fragments electrophoresed on a 0.7% agarose gel. Fragments in the 9-15 kb size range were excised, extracted from the gel, treated with alkaline phosphatase, and ligated to the BamHI arms of the replacement vector lambda GEM11 (Promega Biotec). Recombinant phage were selected by plating on *E. coli* strain ER1793 (New England Biolabs, Mass.). Construction of *H. pylori* genomic library in lambda ZapII vector was as described before(15).

Cloning of cagB, C genes

The region upstream to cagA was used to screen the lambda GEM11 library. Recombinant plaques were transferred to nitrocellulose membranes and hybridized to an upstream cagA probe. The probe was a gel-purified 0.4 kb BglII-EcoRI fragment from pMC3 (15) specific for the upstream region of cagA and was radiolabeled by primer extension using random hexameric oligonuclotides (22). Hybridization was carried out at 68° C. as described previously (15). Positive plaques were purified and recombinant lambda DNA was prepared as described (20). Restriction enzyme cleavage maps were generated and a 4.5 kb BamHI-XhoI fragment carrying the upstream region of cagA was subcloned into pBluescript to create pMT1 (FIG. 1). To further localize the cagA upstream region, pMT1 DNA was cleaved with various restriction endonucleases and compared with the restriction map of the construct (pUT2) containing cagA. A 1.7 kb BglII fragment that contained the cagA upstream region was subcloned into pBluescript to create pMT2.

Southern and colony blot hybridizations

*H. pylori* chromosomal DNA was digested with different restriction endonucleases, and the resulting fragments were electrophoresed on a 0.7% agarose gel. All hybridization conditions and procedures were exactly as described previously(15). For colony blots, *H. pylori* strains were grown on Trypticase soy blood agar plates (BBL), and replica copies of the colonies were transferred to nitrocellulose filters and hybridized with radiolabeled cagB,C probes as described previously (15).

Characterization of *H. pylori* cagB, C genes

To more precisely characterize the structure of upstream region of cagA, we determined its nucleotide sequence from pMT2, using oligonucleotide primers. Translation of the nucleotide sequence of a 1770-bp pMT2 insert in all possible reading frames on both strands revealed an open reading frames of 966 and 600 nucleotides. The first ORF (called cagB) encodes a polypeptide of 322 amino acids, yielding a predicted protein with a molecular weight of 36,043 daltons. A putative signal sequence which contained two possible cleavage sites was identified in the first ORF. This cleavage site between amino acids 22 and 23 is typical of leader sequences of secreted proteins which are cleaved by signal peptidaseI. This was preceded by the sequence which bears resemblance to the consensus cleavage sequence of known lipoproteins. The second ORF (cagC) begins 7 bp of the cagB translational stop codon and it continues to the end of the insert, a result indicating that the second ORF is truncated. A potential ribosome binding site ends 5 bp upstream of cagB. A putative ribosomal binding site is also identified 4 bp upstream of cagC which begins with valine (GTG) as the initiation codon. The sequence 90 bp upstream of the cagB translational start site exhibits the promoter sequence TTTGAT (SEQ ID Nos:1–4), which resembles the Pribnow consensus promoter sequence. This putative −10 region is associated with a −35 region (TTGTCA) that shares 5 of 6 bases with corresponding consensus sequence.

Next, the 0.7 kb region downstream to pMT2 that was mapped in pMT1 (FIG. 1) underwent sequence analysis by use of oligonucleotide primers based on experimentally derived sequences. Translation of this sequence indicated that the second ORF (cagC) still continued.

Cloning and sequencing of the full-length cagC gene

To isolate the full-length gene, we next used the 0.9 kb BglII-XhoI fragment of pMT1 as a probe to screen the lambda ZapII library of *H. pylori* 84–183. Two positive plaques were purified, and the pBluescript plasmids containing the cloned DNA inserts were excised by coinfection with helper phage. The two clones contained DNA inserts of 1.7 kb (pMT3) and 2.1 kb (pMT4). Restriction maps were generated for both pMT3 and pMT4 (FIG. 1), and plasmid pMT4 was selected for sequence analysis. Using forward and reverse primers of the known pBluescript flanking sequences, as well as other primers based on known sequences, the 2060 bp sequence of the pMT4 insert was determined on both strands. As expected, the bases of this sequence (SEQ ID Nos:1–4), beginning with nucleotide 2496) overlapped with the end of the pMT1 sequence. Translation of nucleotide sequence generated from pMT1 and pMT4 revealed that the cagC is 2661 nucleotides long terminated by a TGA codon at position 3830. cagC encodes a protein of 887 amino acid residues, and the calculated molecular weight of the deduced polypeptide is 100,915. A sequence that could form a potential stem-loop structure (G=−6.3) in the mRNA and that could serve as a transcription termination site extends from nucleotides 3844 to 3874 (SEQ ID Nos:1–4). There is no evidence of other ORFs downstream of cagC in the 155 bp that has been sequenced. The full length cagB gene can be obtained using this technique.

Analysis of the cagB,C gene products

To elucidate the function of these cloned genes, the translated amino acid sequence was compared with data bases using FastA and FastDB as well as the BLAST network service of the National Center for Biotechnology Information (Bethesda, Md.). The homology search with CagB did not reveal any striking overall homology with other known sequences. BESTFIT (32) was used to compare CagC with the *Bordetella pertussis* toxin secretion protein (PtlC), SwissProt Accession No. B47301. CagC showed significant homology (26% identity and 50% similarity) with PtlC (26). This homology with PtlC was observed throughout the molecule with several regions of identity extending more than 6 amino acids. In addition, a perfect ATP/GTP binding site was identified at positions 597–605 in the deduced CagC (SEQ ID NO:4), which is also present in ptlC. These studies suggest that the CagC may be involved in toxin secretion.

Conservation of cagB, C genes

To determine whether other *H. pylori* strains possess the cagB or cagC genes or homologous sequences, we studied 55 strains by colony hybridization with pMT2 insert as a probe. A positive signal was obtained from 37 (67.2 %) of these strains (Table 1). Each of these 37 strains also are cagA positive (11 isolates are from patients with duodenal ulceration and 26 isolates are from patients with chronic superficial gastritis alone). The cagB and cagC genes were not present in the 18 cagA negative strains. All 19 strains producing the cytotoxin showed hybridization to pMT2 insert (cagB, C), whereas all 18 strains negative for cagB, C (isolated from patients with gastritis) are negative for cytotoxin production (Table 1). Seven cytotoxin negative strains of *H. pylori* possess the cagB and C genes.

EXAMPLE 2 cagB⁻ and cagC⁻ *H. pylori* Mutants

Construction of cagB and cagC mutant *H. pylori*

To study the role of the CagB and CagC proteins of *H. pylori* in virulence, toxin secretion, and antigenicity, the cagB and cagC genes were inactivated. A *Campylobacter coli* kanamycin resistance gene (23) was ligated into the unique BclI site of plasmid pMT2 that contained the cagB open reading frame to create pMT2:km. The kanamycin resistance gene was inserted into the unique BglII site of pMT3 that contained the 1693 nucleotides of the 2,661-bp cagC open reading frame to create pMT3:km. To inactivate the cagB and cagC genes of *H. pylori*, the constructs pMT2:km and pMT3:km, that are unable to replicate in *H. pylori*, were introduced separately, directly into *H. pylori* 84–183 by electroporation, as described previously (24). Transformants were selected on blood agar plates containing kanamycin (40 µg/ml) and the mutants were characterized by Southern hybridizations for kanamycin insertion in the cagB or cagC genes.

Genotypic characterization of the transformants

To provide genetic evidence that the cagB or cagC gene was disrupted in the transformed strains, DNA isolated from wild-type strain 84–183 and *H. pylori* mutants 84–183:pMT2:km and 84–183:pMT3:km was digested with the restriction endonucleases HindIII, or BglII. After separation of the digested DNA on an agarose gel, the DNA was transferred to a nylon membrane and hybridized to a cagB (pMT2 insert) or cagC (pMT3 insert) probe. The cagB probe hybridized to approximately 1.7 kb and 2.5 kb BglII fragments in the wild-type strain. The 1.7 kb fragment was lost and a new 3.1 kb hybridizing fragment was observed in mutant strain without disruption of the 2.5 kb band. Similarly, the cagC probe hybridized to two bands (2.5 and 3.6 kb) in the wild-type strain whereas in the cagC mutant the 2.5 kb HindIII fragment was lost and a new band (3.6 kb, comigrated with the other 3.6 kb band) was observed. The kanamycin gene probe hybridized only with the 3.1 kb BglII and 3.6 kb HindIII fragment in the mutant strains. These data indicate that as expected, the 10 cagB or cagC genes in 84–183:pMT2:km, and 84–183:pMT3:km, respectively, had been interrupted by the km cassette. The result was insertion of km by homologous recombination of flanking sequences within either cagB or cagC.

TABLE 1

Correlation between the presence of cagB,C genes in *H. pylori*, cagA status, in vitro cytotoxin production and their association with gastritis and duodenal ulcers in 55 patients

| | | | Number of strains | | |
|---|---|---|---|---|---|
| Presence of cagB, C[a] | Presence of cagA[b] | Cytotoxin production[c] | Gastritis[d] (n = 44) | Duodenal ulcer[e] (n = 11) | Total |
| + | + | + | 19 | 8 | 27 |
| + | + | − | 7 | 3 | 10 |
| − | − | − | 18 | 0 | 18 |

[a]As determined by colony blots
[b]As determined by colony blots
[c]As determined in vitro in tissue culture assay
[d]Dyspeptic patient with chronic superficial gastritis only
[e]Dyspeptic patient with duodenal ulcer observed on endoscopy

EXAMPLE 3

CagB/C Operon of *H. pylori* Required for IL-8 Induction in Gastric Cells

Cell culture

Human gastric cancer cell line AGS (ATCC CRL 1739) (26) obtained from American Type Culture Collection (Rockville, Md.), was maintained in RPMI-1640 medium supplemented with 5% fetal calf serum (FCS) (Hyclone Laboratory, Logan, Utah), 20 µg gentamicin/I, 10 mM Hepes buffer, 2 mM glutamine. Fifty-milliliter flasks (Falcon, Becton Dickinson, Lincoln Park, N.J.) were seeded with stock cultures of the above cell line taken from liquid nitrogen and incubated at 37° C. in an ambient atmosphere with 5% $CO_2$ until cells were confluent. The cells then were removed from the flasks by 0.05% trypsin-EDTA treatment (GIBCO BRL, Gaithersburg, Md.) for 10 minutes at room temperature, harvested by centrifugation at 200 g for 10 min, the supernatant discarded, and the cells resuspended in RPMI with 5% FCS. The cell suspension was diluted in fresh media to a final concentration of $1 \times 10^5$ cells per ml and seeded into 6-well tissue culture plates (Costar) and allowed to grow 2-3 days to confluency.

Assay for IL-8 induction by epithelial cells

An in vitro epithelial cell model system was used to study IL-8 responses of gastric cells to *H. pylori* stimulation in vitro (27). Briefly, confluent monolayers of AGS gastric cells cultured in 6-well plastic tissue culture dishes were incubated overnight in serum-free medium for all experiments. At the onset of each experiment, media were replaced with either RPMI 1640 alone, or with RPMI containing live bacteria at a concentration of $10^9$ per ml (bacteria to cell ratio, 1000:1), a ratio at saturation levels for *H. pylori* adherence to gastric epithelial cells (28). Supernatants were removed from the wells at the time intervals described for each experiment and centrifuged at 15,000 g before freezing at −70° C. until further analysis of IL-8 protein by ELISA. The cells were harvested directly into guanidine thiocyanate lysis buffer (Tri-reagent) for preparation of mRNA and subsequent cDNA synthesis. Since IL-8 mRNA expression had peaked after 3 hours of incubation of *H. pylori* in AGS cells (27), IL-8 mRNA induction at this time point by *H. pylori* wild-type strains and isogenic mutants lacking expression of either cagA (U.S. Ser. No. 08/053,614 or cagB (Example 2) or cagC (Example 2) was studied.

RNA preparation

Total cellular RNA was extracted from epithelial cells with Tri-reagent as previously described (29), and quantitation of the purified RNA was performed by absorbance at 260 nM. Briefly, $1-2 \times 10^6$ cells grown in monolayers were directly lysed with Tri-reagent followed by phase separation using chloroform. Following centrifugation at 12,000 g, the RNA, which exclusively remains in the aqueous phase, was removed and precipitated with isopropanol. The RNA pellet obtained after centrifugation at 12,000 g was washed in 75–80% ethanol and subsequently centrifuged at 12,000 g. The RNA pellet obtained was air-dried and resuspended in 15 µl diethyl procarbonate-treated water at 37° C. for 15–20 min.

Reverse transcription (RT) and PCR cDNA was synthesized from 2 µg of total RNA obtained from cultured human epithelial cells, by priming with 1 µg of an oligo dT primer, 200 nmol of each dNTP, 20 units of RNAse inhibitor and RNAseH⁻ MMLV reverse transcriptase (BRL, Gaithersburg, Md.) at 100 u/µg RNA in a final volume of 25 µl at 42° C. for 1 h. cDNA equivalent to 80 ng of starting RNA was used for each PCR reaction with primers for human IL-8 or control human glyceraldehyde-3-phosphate dehydrogenase (GAPDH) (ClonTech, Palo Alto, Calif.). Primers used were as follows GAPDH: sense-5'TGAAGGTCGGAGTCAACGGATTTGGT (SEQ ID NO:5); antisense 5'CATGTTGAGGTCCACCAC (SEQ ID NO:6); IL-8: sense-5'ATGACTTCCAAGCTGGC-CGTGGC (SEQ ID NO:7); antisense-5'TCTCAGCCCTCT-TCAAAAACTTCTC (SEQ ID NO:8). PCR reactions were performed in 10 mM Tris/HCl, pH 8.3, 50 mM KCl, 1.5 mM $MgCl_2$, 0.2 mM dNTP, and 2 units of Taq polymerase (Perkin Elmer Cetus, Norwalk, Conn.). Primers were added at a final concentration of 0.5 mM. Reactions were carried out in a DNA Thermal Cycler (Perkin Elmer Cetus) for 30 (IL-8) or 39 cycles (GAPDH), including denaturing at 94° C. for 1 min, annealing at 60° C. for 1 min, and extension at 72° C. for 2 min for each cycle. PCR products were analyzed on ethidium bromide-stained 2% agarose gels. To control for false-positive results due to contaminating genomic DNA, primers were used for RT-PCR of mRNA for GAPDH and IL-8 that spanned introns, based on the published genomic DNA sequences for these genes (30,31). In this manner, if the primers amplify genomic DNA, the resulting amplified product will be of a larger size than products amplified from cDNAs that lack the intron. In the experiments reported, the sizes of the amplified product were those predicted for amplification of cDNA and no larger products were seen. All PCR experiments included a positive control and a negative control without template to assure absence of contamination.

Expression of IL-8 by wild-type and mutant *H. pylori* strains

Amplification of the cDNA from AGS cells incubated with the wild type or mutant strains with primers for GAPDH demonstrated that expression of transcript for this constitutive enzyme was essentially identical for all cultures. The cagA⁻ mutants of *H. pylori* induced AGS cells to express IL-8 mRNA to a comparable extent as the parental wild type strains, confirming our earlier observations (27). In contrast, cagB⁻ or cagC⁻ mutants of strain 84–183 were significantly decreased in IL-8 mRNA expression by AGS cells. For strain 60190, the cagB⁻ or cagC⁻ mutants showed no detectable induction of IL-8 mRNA expression by AGS cells.

IL-8 protein assay

IL-8 protein levels in cell culture supernatants were determined by use of a human IL-8 sandwich enzyme-linked immunosorbent assay kit (R&D Systems, Minneapolis, Minn.) and expressed as picograms per milliliter. The lower limit of detection for IL-8 was 32 pg/ml. Differences between cytokine levels were evaluated by Student's T-test and were considered significant when p was <0.05.

Figure 2:
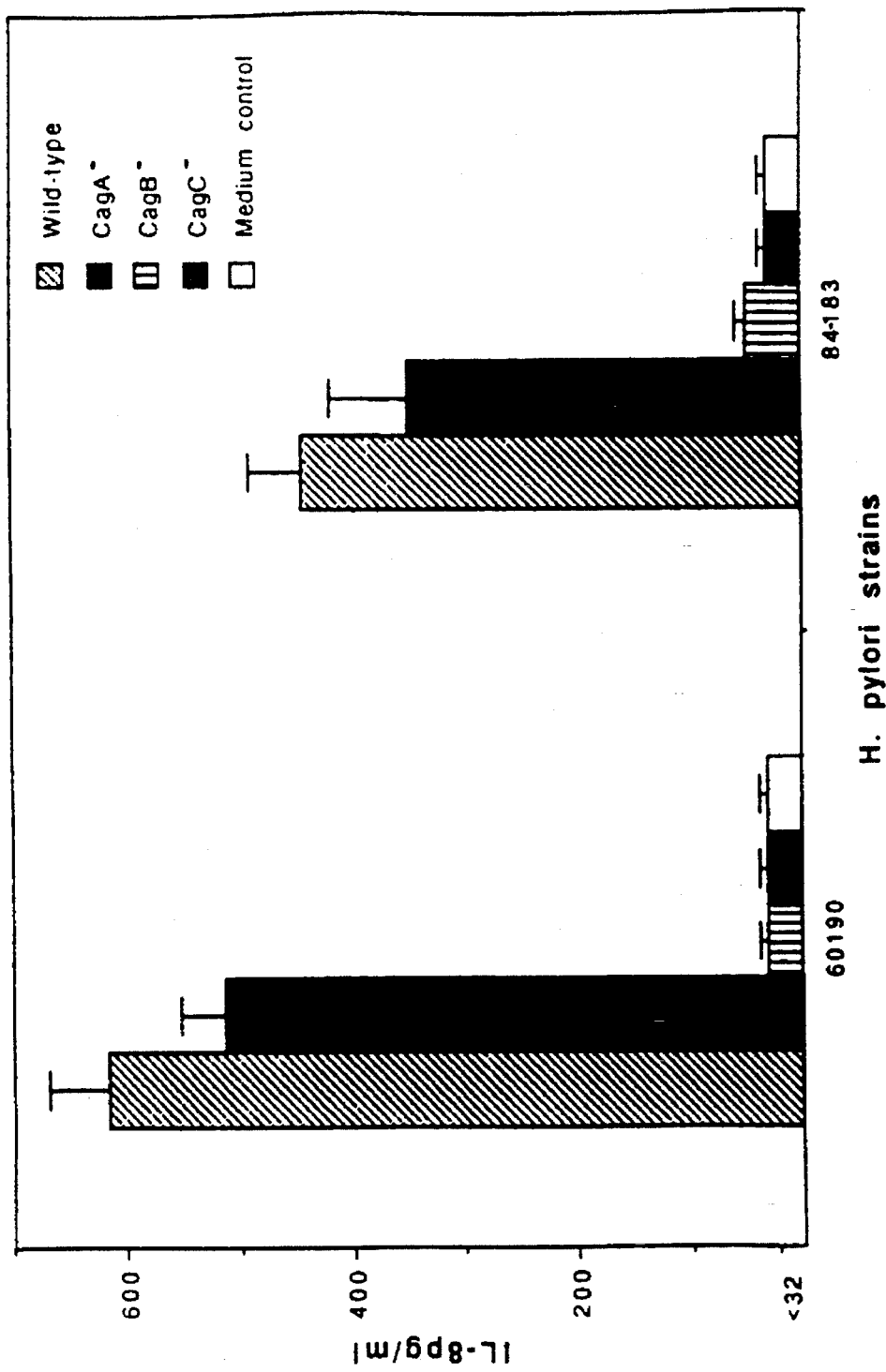
FIG. 2 shows the kinetics of IL-8 induction in AGS cells by live *H. pylori* wild-type strains (60190 and 84–183) and mutants of those strains. IL-8 protein levels in culture supernatants from AGS epithelial cells after stimulation with viable *H. pylori* cells at 6 hours were measured by ELISA; results shown are Mean±SEM of 3 or 4 replicate determinations.

Examination of AGS cell secretion of IL-8 into culture supernatants, demonstrated that there was little difference between the wild type and cagA⁻ mutant for either strain 84–183 or 60190 (FIG. 2). However, the cagB⁻ and cagC⁻ mutants induced significantly (p<0.002) less IL-8 secretion by AGS cells than did the wild type cells (FIG. 2).

These data clearly demonstrate the role of mutation in cagB or cagC in reducing *H. pylori*-induced transcription and translation of IL-8 by AGS cells.

Throughout this application various publications are referenced by numbers within parentheses. Full citations for these publications are as follows. The disclosures of these publications in their entireties are hereby incorporated by reference into this application in order to more fully describe the state of the art to which this invention pertains.

REFERENCES

1. Marshall, B. J., Warren, J. R. 1984. Unidentified curved bacilli in the stomach of patients with gastritis and peptic ulceration. Lancet i:1311–14
2. Blaser, M. J. 1990. *Helicobacter pylori* and the pathogenesis of gastroduodenal inflammation. J. Infect. Dis. 161:626–633.
3. Blaser M. J. Hypotheses on the pathogenesis and natural history of *Helicobacter pylori*-induced inflammation. Gastroenterol. 1992;102:720–727.
4. Peterson, W. L. 1991. *Helicobacter pylori* and peptic ulcer disease. N. Engl. J. Med. 324:1043–48
5. Walker, I. R., Strickland, R. G., Ungar, B., Mackay, I. R. 1971. Simple atrophic gastritis and gastric carcinoma. Gut 12:906–11
6. Parsonnet, J., Vandersteen, D., Goates, J., Sibley, R. K., Pritikin, J., and Y. Chang. 1991. Helicobacter pylori infection in intestinal- and diffuse-type gastric adenocarcinomas. J. Nat. Cancer Inst. 83:640–643.
7. Nomura, A., Stemmermann, G. N., Chyou, P. -H., Perez-Perez, G. I., and M. J. Blaser. 1991. *Helicobacter pylori* infection and gastric carcinoma in a population of Japanese-Americans in Hawaii. N. Engl. J. Med. 325:1132–1136.
8. Talley, N. J., Zinsmeister, A. R., Weaver, A., DiMagno, E. P., Carpenter, H. A., Perez-Perez, G. I., and M. J. Blaser. 1991. Gastric adenocarcinoma and *Helicobacter pylori* infection. J. Nat. Cancer Inst. 83:1734–1739.
9. Rauws, E. A. J., Tytgat, G. N.J. 1990. Cure of dudenal ulcer associated with eradication of *Helicobacter pylori*. Lancet 335:1233–1235
10. Leunk, R. D., Johnson, P. T., David, B. C., Kraft, W. G., Morgan, D. R. 1988. Cytotoxic activity in broth-culture filtrates of *Campylobacter pylori*. J. Med. Microbiol. 26:93–99
11. Figura, N., Guglielmetti, P., Rossolini, A., Barberi, A., Cusi, G., Musmanno, R., Russi, M., and S. Quaranta. 1989. Cytotoxin production by *Campylobacter pylori* strains isolated from patients with peptic uclers and from patients with chronic gastritis only. J. Clin. Microbiol. 27:225–226.
12. Cover, T. L., C. P. Dooley, and M. J. Blaser. 1990. Characterization of human serologic response to proteins in *Helicobacter pylori* broth culture supernatants with vacuolizing cytotoxin activity. Infect. Immun. 58:603–610.
13. Crabtree, J. E., J. D. Taylor, J. I. Wyatt, R. V. Heatley, T. M. Shallcross, D. S. Tompkins, and B. J. Rathbone. 1991. Mucosal IgA recognition of *Helicobacter pylori* 120 kDa protein, peptic ulceration and gastric pathology. Lancet 338:332–335.
14. Crabtree, J. E., N. Figura, J. D. Taylor, M. Bugnoli, D. Armellini, and D. S. Tompkins. 1992. Expression of 120 kilodalton protein and cytotoxicity in *Helicobacter pylori*. J. Clin. Pathol. 45:733–734.
15. Tummuru, M. K. R., T. Cover, and M. J. Blaser. 1993. Cloning and expression of a high molecular mass major antigen of *Helicobacter pylori:* Evidence of linkage to cytotoxin production. Infect. Immun. 61:1799–1809.
16. Covacci, A., S. Censini, M. Bugnoli, R. Petracca, D. Burroni, G. Macchia, A. Massone, E. Papini, Z. Xiang, N. Figura, and R. Rappuoli. 1993. Molecular characterization of the 128 kDa immunodominant antigen of *Helicobacter pylori* associated with cytotoxicity and duodenal ulcer. Proc. Natl. Acad. Sci. USA. 90:5791–5795.
17. Peek, R. M., Blaser M. J., and Miller G. G. 1994. cagA-positive *Helicobacter pylori* strains induce preferential cytokine expression in gastric mucosa. Abstract presented at Americal Gastroenterological Association Meetings. Neworleans, La.
18. Noach, L. A., Bosma, N. B., Jansen J., Hoek, F. J., Deventer S.. J. H. V., and Tytgat G. N. J. 1994. Mucosal Tumor necrosis factor-alpha, interleukin-1 beta, and interleukin-8 production in patients with Helicobacter pylori infection. 425–429.
19. Birnboim, N. C., and J. Doly. 1979. A rapid alkaline extraction procedure for screening recombinant plasmid DNA. Nucleic Acids Res. 7:1513–1523.

20. Maniatis, T., E. F. Fritsch, and J. Sambrook. 1989. Molecular cloning; a laboratory manual. Cold Spring Harbor Laboratory, Cold Spring Harbor, N.Y.

21. Sanger, F., S. Nicklen, and A. R. Coulson. 1977. DNA sequencing with chain-terminating inhibitors. Proc. Natl.Acad. Sci. USA 74:5463–5467.

22. Feinberg, A. P., and B. Vogelstein. 1983. A technique for radiolabeling DNA restriction endonuclease fragments to high specific activity. Anal.Biochem. 132:6–13.

23. Labigne-Roussel, A., Harel, J., and L. Tompkins. 1987. Gene transfer from *Escherichia coli* to *Campylobacter* species. Development of shuttle vectors for genetic analysis of *Campylobacter jejuni*. J. Bacteriol. 169:5320–5323.

24. Ferrero, R. L., V. Cussac, P. Courcoux, and A. Labigne. 1992. Construction of isogenic urease-negative mutants of *Helicobacter pylori* by allelic exchange. J. Bacteriol. 174:4212–4217.

25. Weiss, A. A., Johnson F. D., and Burns D. L. 1993. Molecular characterization of an operon required for pertussis toxin secretion. Proc.Natl.Acad. Sci.USA. 90:2970–2074.

26. Barranco, S. C., Townsend J. C. M., Quarishi M. A., et al. 1983. Heterogenous responses of an in vitro model of stomach human cancer to anticancer drugs. Investigational New Drugs 1:117–127.

27. Sharma, S. A., Tummuru M. K. R., Miller G. G., Blaser M. J. Interleukin-8 response of gastric epithelial cell lines to Helicobacter pylori stimulation in vitro, Am. J. Gastroenterol. 1994; 89:1346.

28. Dunn, B. E., Altmann M., Campbell G. P. Adherence of *Helicobacter pylori* to gastric carcinoma cells: analysis by flow cytometry. Rev. Infect. Dis. 1991;13 Suppl 8:S657–S664.

29. Chomczynski P. A reagent for the single-step simultaneous isolation of RNA, DNA and proteins from cell and tissue samples. Bio Techniques 1993;15:532–537.

30. Ercolani, L., Florence B. Denaro M., Alexander M. 1988. Isolation and complete sequence of a functional human glyceraldehyde-3-phosphate dehydrogenase gene. J. Biol. Chem. 263:15335–15341.

31. Mukaida, N., Murakami S., Matsushima K. 1989. Genomic structure of the human monocyte-derived neutrophil chemostatic factor IL-8. J. Immunol. 143:1366–1371.

32. Smith, T. R. and Watermam, M. S. 1981. Advances in Applied Mathematics 2:482–489.

33. Donnenberg, M. S. and Kaper, J. B. Construction of an eae deletion mutant of enteropatyhogenic *Escherichia coli* by using a positive-selection suicide vector. Infect. Immun. 1991:4310–4317.

34. Harlow and Lane, *Antibodies; A Laboratory Manual*, Cold Spring Harbor Laboratory, Cold Spring Harbor, N.Y., 1988.

35. Arnon, R. (Ed.) *Synthetic Vaccines* I:83–92, CRC Press, Inc., Boca Raton, Fla., 1987.

---

What is claimed is:

1. An isolated nucleic acid encoding a polypeptide consisting of amino acids 1 through 322 in the sequence set forth as SEQ ID NO:1.

2. The nucleic acid of claim 1 in a vector suitable for expressing a polypeptide encoded by the nucleic acid.

3. The isolated nucleic acid of claim 1, wherein the nucleic acid consists of nucleotides 193 through 1158 in the sequence set forth as SEQ ID NO:1.

4. The nucleic acid of claim 3 in a vector suitable for expressing a polypeptide encoded by the nucleic acid.

5. An isolated nucleic acid that hybridizes with the nucleic acid of claim 4 under polymerase chain reaction conditions of 30–40 cycles of about 2 min of denaturation, about 1 min of annealing, and about 1 min of extension, followed by an extension step of about 5 min, with temperatures of about 94° C. for denaturation, about 60° C. for annealing, and about 72° C. for extension.

6. An isolated nucleic acid that hybridizes with the nucleic acid of claim 4 under the stringency conditions of 68° C. for 16 hours in buffer containing 6 X SSC, 0.5% sodium dodecyl sulfate, 5 X Denhardt's solution and 100 µg salmon sperm DNA, with washing at 60° C. in 0.5 X SSC.

7. The nucleic acid of claim 6, which encodes a functional CagB polypeptide, in a vector suitable for expressing a polypeptide encoded by the nucleic acid.

8. An isolated nucleic acid encoding a polypeptide consisting of amino acids 1 through 887 in the sequence set forth in SEQ ID NO:3.

9. The nucleic acid of claim 8 in a vector suitable for expressing a polypeptide encoded by the nucleic acid.

10. The isolated nucleic acid of claim 8, wherein the nucleic acid consists of nucleotides 1170 through 3830 in the sequence set forth as SEQ ID NO:3.

11. The nucleic acid of claim 10 in a vector suitable for expressing a polypeptide encoded by the nucleic acid.

12. An isolated nucleic acid that hybridizes with the nucleic acid of claim 10 under polymerase chain reactions of 30–40 cycles of about 2 min of denaturation, about 1 min of annealing, and about 1 min of extension, followed by an extension step of about 5 min, with temperatures of about 94° C. for denaturation, about 60° C. for annealing, and about 72° C. for extension.

13. An isolated nucleic acid that hybridizes with the nucleic acid of claim 10 under the stringency conditions of 68° C. for 16 hours in buffer containing 6 X SSC, 0.5% sodium dodecyl sulfate, 5X Denhardt's solution and 100 µg salmon sperm DNA, with washing at 60° C. in 0.5 X SSC.

14. The nucleic acid of claim 13, which encodes a functional CagC polypeptide, in a vector suitable for expressing a polypeptide encoded by the nucleic acid.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3989 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 193..1158

( x i ) SEQUENCE DESCRIPTION: SEQ ID NO:1:

```
ATCTACAATT  CTACGATGAC  TTGAGAAAGA  AAAATGGTTG  GGACAAGTAG  GTTTATTGTT              60

CCTAAATTAT  ATCAGTTGTC  AAACAAAAGC  GTCGGTTTTG  ATTTAAATTA  TAAAGTAGCG             120

CTTGTATGAA  TAGTATAAAA  ATACTTTTTT  TTGATATACT  CAAACGATTG  ATTTCAATTT             180

GAAAGGAAAC GC ATG AAA TTT TTT ACA AGA ATC ACT GAC AGC TAC AAG                     228
              Met Lys Phe Phe Thr Arg Ile Thr Asp Ser Tyr Lys
               1               5                  10

AAA GTT GTA GTA ACT TTA GGG CTA GCG ATA GCA GCC AAT CCT TTA ATG                   276
Lys Val Val Val Thr Leu Gly Leu Ala Ile Ala Ala Asn Pro Leu Met
         15                  20                  25

GCT TTC GAC AGT CCT GCA TCA GGC ATT ACT GAG ACT AAA ACT TTG GTG                   324
Ala Phe Asp Ser Pro Ala Ser Gly Ile Thr Glu Thr Lys Thr Leu Val
         30                  35                  40
```

| | | | | | | | | | | | | | | | | |
|---|---|---|---|---|---|---|---|---|---|---|---|---|---|---|---|---|
|GTT|CAG|ATC|ATT|TCT|GTT|CTA|GCG|ATC|GTA|GGT|GGT|TGC|GCT|CTA|GGA|372|
|Val|Gln|Ile|Ile|Ser|Val|Leu|Ala|Ile|Val|Gly|Gly|Cys|Ala|Leu|Gly| |
|45| | | | |50| | | |55| | | | |60| | |
|GTC|AAA|GGT|ATA|GCG|GAT|ATT|TGG|AAA|ATC|TCT|GAT|GAC|ATC|AAA|AGA|420|
|Val|Lys|Gly|Ile|Ala|Asp|Ile|Trp|Lys|Ile|Ser|Asp|Asp|Ile|Lys|Arg| |
| | | | |65| | | |70| | | | |75| | | |
|GGT|CAA|GCG|ACT|GTT|TTT|GCT|TAC|GCG|CAG|CAT|AGC|TAT|GTT|AGC|GGT|468|
|Gly|Gln|Ala|Thr|Val|Phe|Ala|Tyr|Ala|Gln|His|Ser|Tyr|Val|Ser|Gly| |
| | | |80| | | | |85| | | | |90| | | |
|GGC|GGT|GGC|ATT|ATC|TAT|TTG|AGC|ACT|AAG|TTT|GGC|TTC|AGT|ATT|GGC|516|
|Gly|Gly|Gly|Ile|Ile|Tyr|Leu|Ser|Thr|Lys|Phe|Gly|Phe|Ser|Ile|Gly| |
| | |95| | | | |100| | | | |105| | | | |
|GGA|ACG|GAG|GAG|CTA|GCT|AAA|TTG|ATC|AAT|AAT|AAT|AGT|AAT|AAA|AAA|564|
|Gly|Thr|Glu|Glu|Leu|Ala|Lys|Leu|Ile|Asn|Asn|Asn|Ser|Asn|Lys|Lys| |
|110| | | | |115| | | | |120| | | | | | |
|CTG|AGA|GGC|TTT|TTT|TTG|AAA|GTT|CTC|TTA|GGT|CTC|GTT|GTT|TTC|AGT|612|
|Leu|Arg|Gly|Phe|Phe|Leu|Lys|Val|Leu|Leu|Gly|Leu|Val|Val|Phe|Ser| |
|125| | | | |130| | | | |135| | | | |140| |
|TCG|TAT|GGG|TCA|GCC|AAT|GAT|GAT|AAA|GAA|GCC|AAA|AAA|GAA|GCA|CAA|660|
|Ser|Tyr|Gly|Ser|Ala|Asn|Asp|Asp|Lys|Glu|Ala|Lys|Lys|Glu|Ala|Gln| |
| | | | |145| | | | |150| | | | |155| | |
|GAA|AAA|GAA|ATA|AAC|ACT|CCC|AAT|GGG|CGT|GTT|TAT|ACG|AAT|TTA|GAT|708|
|Glu|Lys|Glu|Ile|Asn|Thr|Pro|Asn|Gly|Arg|Val|Tyr|Thr|Asn|Leu|Asp| |
| | | |160| | | | |165| | | | |170| | | |
|TTT|GAT|AGT|TTC|AAA|GCG|ACT|ATC|AAA|AAT|TTG|AAA|GAC|AAG|AAA|GTA|756|
|Phe|Asp|Ser|Phe|Lys|Ala|Thr|Ile|Lys|Asn|Leu|Lys|Asp|Lys|Lys|Val| |
| | |175| | | | |180| | | | |185| | | | |
|ACT|TTC|AAA|GAA|ATC|AAT|CCC|GAT|ATT|ATC|AAA|GAT|GAA|GTT|TTT|GAT|804|
|Thr|Phe|Lys|Glu|Ile|Asn|Pro|Asp|Ile|Ile|Lys|Asp|Glu|Val|Phe|Asp| |
|190| | | | |195| | | | |200| | | | | | |
|TTC|GTG|ATT|GTC|AAT|AGA|GTC|CTT|AAA|AAA|ATA|AAG|GAT|TTG|AAG|CAT|852|
|Phe|Val|Ile|Val|Asn|Arg|Val|Leu|Lys|Lys|Ile|Lys|Asp|Leu|Lys|His| |
|205| | | | |210| | | | |215| | | | |220| |
|TAC|GAT|CCC|ATT|ATT|GAA|AAA|ATC|TTT|GAT|GAA|AAG|GGT|AAA|GAA|ATG|900|
|Tyr|Asp|Pro|Ile|Ile|Glu|Lys|Ile|Phe|Asp|Glu|Lys|Gly|Lys|Glu|Met| |
| | | | |225| | | | |230| | | | |235| | |
|GGA|CTG|AAT|GTA|GAA|TTA|CAG|ATC|AAT|CCT|GAA|GTG|AAA|GAC|TTT|TTT|948|
|Gly|Leu|Asn|Val|Glu|Leu|Gln|Ile|Asn|Pro|Glu|Val|Lys|Asp|Phe|Phe| |
| | | |240| | | | |245| | | | |250| | | |
|ACT|TTC|AAA|AGC|ATC|AGC|ACG|ACC|AAC|AAA|CAA|CGC|TGC|TTT|CTG|TCA|996|
|Thr|Phe|Lys|Ser|Ile|Ser|Thr|Thr|Asn|Lys|Gln|Arg|Cys|Phe|Leu|Ser| |
| | |255| | | | |260| | | | |265| | | | |
|TTG|CGT|GGG|GAA|ACA|AGA|GAA|ATT|TTA|TGC|GAT|GAT|AAG|CTA|TAC|AAT|1044|
|Leu|Arg|Gly|Glu|Thr|Arg|Glu|Ile|Leu|Cys|Asp|Asp|Lys|Leu|Tyr|Asn| |
|270| | | | |275| | | | |280| | | | | | |
|GTC|TTA|TTG|GCC|GTA|TTC|AAT|TCT|TAT|GAC|CCT|AAT|GAT|CTT|TTG|AAA|1092|
|Val|Leu|Leu|Ala|Val|Phe|Asn|Ser|Tyr|Asp|Pro|Asn|Asp|Leu|Leu|Lys| |
|285| | | | |290| | | | |295| | | | |300| |
|CAT|ATT|AGC|ACC|ATA|GAG|TCT|CTC|AAA|AAA|ATC|TTT|TAT|ACG|ATT|ACA|1140|
|His|Ile|Ser|Thr|Ile|Glu|Ser|Leu|Lys|Lys|Ile|Phe|Tyr|Thr|Ile|Thr| |
| | | | |305| | | | |310| | | | |315| | |
|TGT|GAA|GCG|GTG|TAT|CTA|TAAAGAGAGG|GGTGTTTGTG|GCAAGCAAGC| | | | | | | |1188|
|Cys|Glu|Ala|Val|Tyr|Leu| | | | | | | | | | | |
| | | |320| | | | | | | | | | | | | |

AGGCTGATGA ACAAAAAAAG CTAGTTATAG AGCAAGAGGT TCAAAAACGG CAGTTTCAAA    1248

AAATAGAAGA ACTTAAAACA GACATGCAAA AAGGTATTAA TCCCTTTTTT AAAGTCTTGT    1308

TTGATGGGGG GAATAGGTTG TTTGGTTTCC CTGAAACTTT TATTTATTCC TCCATATTTA    1368

TATTGTTTGT AACAATTGTA TTATCTGTTA TTCTTTTTCA AGCCTATGAA CCTGTTTTGA    1428

```
TTGTAGCGAT TGTTATTGTG CTTGTAGCTC TTGGATTCAA GAAAGATTAC AGGCTTTATC    1488
AAAGAATGGA GCGAGCGATG AAATTTAAAA AACCTTTTTT GTTTAAGGGC GTGAAAAACA    1548
AAGCGTTCAT GAGCATTTTT TCCATGAAGC CTAGTAAAGA AATGGCGAAT GACATCCACT    1608
TAAATCCAAA CAGAGAAGAC AGACTTGTGA GCGCTGCAAA TTCCTATCTA GCGAATAACT    1668
ATGAATGTTT TTTAGATGAT GGGGTGATCC TTACTAACAA CTATTCTCTT TTAGGCACAA    1728
TCAAATTGGG GGGCATTGAT TTTTTAACCA CTTCCAAAAA AGATCTCATA GAGTTACACG    1788
CTTCTATTTA TAGCGTTTTT AGGAATTTG TTACCCCTGA ATTCAAATTT TATTTTCACA     1848
CTATTAAAAA GAAAATCGTT ATTGATGAAA CCAATAGGGA TTATGGTCTT ATTTTTTCTA    1908
ATGATTTCAT GCGAGCCTAT AATGAGAAGC AAAAGAGAGA AGTTTTTAT GATATTAGTT     1968
TTTATCTCAC CATAGAGCAA GATTTATTAG ACACTCTCAA TGAACCCGTT ATGAATAAAA    2028
AGCATTTGC AGATAATAAT TTTGAAGAGT TTCAAAGGAT TATTAGAGCC AAGCTTGAAA     2088
ACTTCAAGGA TAGGATAGAG CTTATAGAAG AGCTACTGAG TAAATACCAC CCCACTAGAT    2148
TGAAAGAATA CACCAAAGAT GGCATTATTT ATTCCAAACA ATGCGAGTTT TATAATTTTT    2208
TGGTGGGAAT GAATGAAGCC CCTTTTATTT CGAACCGAAA AGACTTGTAT CTCAAAGAAA    2268
AAATGCATGG TGGGGTGAAA GAAGTTTATT TTGCTAATAA GCATGGAAAA ATCTTAAATG    2328
ACGATTTGAG TGAAAAATAT TTTAGTGCTA TTGAGATCAG TGAATACGCC CCTAAATCAC    2388
AGAGCGATTT GTTGATAAA ATCAACGCTC TAGACAGCGA ATTTATCTTT ATGCATGCTT     2448
ATTCGCCTAA AAACTCACAA GTTTTAAAGG ACAAACTAGC TTTCACCTCT AGAAGGATTA    2508
TTATTAGTGG AGGCTCCAAA GAGCAAGGCA TGACTTTGGG TTGCTTGAGC GAATTAGTGG    2568
GTAATGGTGA TATTACGCTA GGCAGTTATG GTAATTCTTT AGTGCTGTTT GCTGATAGCT    2628
TTGAAAAAAT GAAACAAAGC GTTAAGGAAT GCGTCTCGAG TCTTAACGCT AAAGGTTTTT    2688
TAGCCAACGC AGCGACTTTC TCTATGGAAA ATTACTTTTT TGCCAAACAT TGCTCTTTTA    2748
TCACGCTTCC TTTTATTTTT GATGTAACTT CTAACAATTT TGCTGATTTC ATAGCGATGA    2808
GAGCGATGAG TTTTGATGGC AATCAAGACA ATAACGCTTG GGCAATAGC GTGATGACGC     2868
TAAAAAGCGA GATCAACTCG CCTTTTATC TCAATTTCCA CATGCCTACT GATTTTGGTT     2928
CAGCTTCAGC AGGACACACT TTGATACTTG GCTCAACCGG TTCAGGTAAA ACAGTGTTTA    2988
TGTCCATGAC TCTAAACGCT ATGGGGCAAT TGCTATAAT TTTCCTGCTA ATGTCAGCAA     3048
AGACAAACAA AAGCCTCACT ATGGTCTATA TGGATAAAGA TTATGGTGCT TATGGGAATA    3108
TTGTCGCAAT GGGTGGGGAG TATGTCAAGA TTGAGCTAGG GACAGATACA GGATTAAATC    3168
CTTTTGCTTG GGCGGCTTGC GTGCAAAAAA CAGATGCAAC AATGGAGCAA AAACAAACGG    3228
CTATTTCTGT TGTCAAAGAG CTTGTGAAGA ACCTAGCGAC CAAAAGCGAT GAAAAAGATG    3288
AAAATGGCAA CAGCGTCTCT TTTAGCCTAG CCGATTCTAA CACGCTTGCA GCGGCAGTAA    3348
CCAACCTTAT CACAGGAGAT ATGAACCTAG ATTATCCCAT CACTCAACTT ATTAACGCTT    3408
TTGGAAAAGA CCACAATGAT CCTAATGGGC TTGTCGCGCG ATTAGCGCCT TTTTGCAAAT    3468
CAACCAATGG TGAATTTCAA TGGCTTTTTG ATAATAAAGC AACAGATCGC TTAGATTTTT    3528
CAAAAACGAT TATTGGCGTT GATGGGTCAA GTTCTTAGA CAATAATGAT GTTTCGCCCT     3588
TTATTTGTTT TTACCTTTTC GCTCGTATCC AAGAGGCAAT GGATGGGCGT AGATTTGTCT    3648
TAGATATTGA TGAAGCGTGG AAATACTTAA GCGATCCAAA GGTCGCTTAT TTTGTAAGAG    3708
ACATGCTAAA AACCGCAAGA AAAGAAACGC TATTGTTAGA CTTGCAACCC AAAGCATCAC    3768
TGATCTTTTG GCTTGCCCTA TTGCTGATAC GATTAGAGAA CAATGCCCTA CAAAGATTTT    3828
```

```
TTTGAGAAAC GATGGGGGTA ATCTTTCTGA TTACCAAAGA TTAGCCAATG TTACAGAAAA      3888

AGAATTTGAA ATCATCACTA AGGGGCTAGA TAGGAAAATC CTCTACAAAC AGGACGGAAG      3948

CCCTAGCGTT ATCGCTAGTT TTAATTTGAG AGGCGCTTCC T                          3989
```

( 2 ) INFORMATION FOR SEQ ID NO:2:

( i ) SEQUENCE CHARACTERISTICS:
        ( A ) LENGTH: 322 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Phe Phe Thr Arg Ile Thr Asp Ser Tyr Lys Lys Val Val Val
 1               5                  10                       15

Thr Leu Gly Leu Ala Ile Ala Ala Asn Pro Leu Met Ala Phe Asp Ser
            20                  25                  30

Pro Ala Ser Gly Ile Thr Glu Thr Lys Thr Leu Val Val Gln Ile Ile
            35                  40                  45

Ser Val Leu Ala Ile Val Gly Gly Cys Ala Leu Gly Val Lys Gly Ile
50                      55                      60

Ala Asp Ile Trp Lys Ile Ser Asp Asp Ile Lys Arg Gly Gln Ala Thr
65                      70                  75                  80

Val Phe Ala Tyr Ala Gln His Ser Tyr Val Ser Gly Gly Gly Gly Ile
                85                  90                      95

Ile Tyr Leu Ser Thr Lys Phe Gly Phe Ser Ile Gly Gly Thr Glu Glu
            100                 105                 110

Leu Ala Lys Leu Ile Asn Asn Asn Ser Asn Lys Lys Leu Arg Gly Phe
            115                 120                 125

Phe Leu Lys Val Leu Leu Gly Leu Val Val Phe Ser Ser Tyr Gly Ser
        130                 135                 140

Ala Asn Asp Asp Lys Glu Ala Lys Lys Glu Ala Gln Glu Lys Glu Ile
145                 150                 155                 160

Asn Thr Pro Asn Gly Arg Val Tyr Thr Asn Leu Asp Phe Asp Ser Phe
                165                 170                 175

Lys Ala Thr Ile Lys Asn Leu Lys Asp Lys Lys Val Thr Phe Lys Glu
            180                 185                 190

Ile Asn Pro Asp Ile Ile Lys Asp Glu Val Phe Asp Phe Val Ile Val
            195                 200                 205

Asn Arg Val Leu Lys Lys Ile Lys Asp Leu Lys His Tyr Asp Pro Ile
    210                 215                 220

Ile Glu Lys Ile Phe Asp Glu Lys Gly Lys Glu Met Gly Leu Asn Val
225                 230                 235                 240

Glu Leu Gln Ile Asn Pro Glu Val Lys Asp Phe Phe Thr Phe Lys Ser
                245                 250                 255

Ile Ser Thr Thr Asn Lys Gln Arg Cys Phe Leu Ser Leu Arg Gly Glu
            260                 265                 270

Thr Arg Glu Ile Leu Cys Asp Asp Lys Leu Tyr Asn Val Leu Leu Ala
    275                 280                 285

Val Phe Asn Ser Tyr Asp Pro Asn Asp Leu Leu Lys His Ile Ser Thr
    290                 295                 300

Ile Glu Ser Leu Lys Lys Ile Phe Tyr Thr Ile Thr Cys Glu Ala Val
305                 310                 315                 320

Tyr Leu
```

(2) INFORMATION FOR SEQ ID NO:3:

(i) SEQUENCE CHARACTERISTICS:
        (A) LENGTH: 3989 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1170..3830

(xi) SEQUENCE DESCRIPTION: SEQ ID NO:3:

```
ATCTACAATT  CTACGATGAC  TTGAGAAAGA  AAAATGGTTG  GGACAAGTAG  GTTTATTGTT      60

CCTAAATTAT  ATCAGTTGTC  AAACAAAAGC  GTCGGTTTTG  ATTTAAATTA  TAAAGTAGCG     120

CTTGTATGAA  TAGTATAAAA  ATACTTTTT   TTGATATACT  CAAACGATTG  ATTTCAATTT     180

GAAAGGAAAC  GCATGAAATT  TTTTACAAGA  ATCACTGACA  GCTACAAGAA  AGTTGTAGTA     240

ACTTTAGGGC  TAGCGATAGC  AGCCAATCCT  TTAATGGCTT  TCGACAGTCC  TGCATCAGGC     300

ATTACTGAGA  CTAAAACTTT  GGTGGTTCAG  ATCATTTCTG  TTCTAGCGAT  CGTAGGTGGT     360

TGCGCTCTAG  GAGTCAAAGG  TATAGCGGAT  ATTTGGAAAA  TCTCTGATGA  CATCAAAAGA     420

GGTCAAGCGA  CTGTTTTTGC  TTACGCGCAG  CATAGCTATG  TTAGCGGTGG  CGGTGGCATT     480

ATCTATTTGA  GCACTAAGTT  TGGCTTCAGT  ATTGGCGGAA  CGGAGGAGCT  AGCTAAATTG     540

ATCAATAATA  ATAGTAATAA  AAAACTGAGA  GGCTTTTTTT  TGAAAGTTCT  CTTAGGTCTC     600

GTTGTTTTCA  GTTCGTATGG  GTCAGCCAAT  GATGATAAAG  AAGCCAAAAA  AGAAGCACAA     660

GAAAAAGAAA  TAAACACTCC  CAATGGGCGT  GTTTATACGA  ATTTAGATTT  TGATAGTTTC     720

AAAGCGACTA  TCAAAAATTT  GAAAGACAAG  AAAGTAACTT  TCAAAGAAAT  CAATCCCGAT     780

ATTATCAAAG  ATGAAGTTTT  TGATTTCGTG  ATTGTCAATA  GAGTCCTTAA  AAAAATAAAG     840

GATTTGAAGC  ATTACGATCC  CATTATTGAA  AAAATCTTTG  ATGAAAAGGG  TAAAGAAATG     900

GGACTGAATG  TAGAATTACA  GATCAATCCT  GAAGTGAAAG  ACTTTTTTAC  TTTCAAAAGC     960

ATCAGCACGA  CCAACAAACA  ACGCTGCTTT  CTGTCATTGC  GTGGGGAAAC  AAGAGAAATT    1020

TTATGCGATG  ATAAGCTATA  CAATGTCTTA  TTGGCCGTAT  TCAATTCTTA  TGACCCTAAT    1080

GATCTTTTGA  AACATATTAG  CACCATAGAG  TCTCTCAAAA  AAATCTTTTA  TACGATTACA    1140

TGTGAAGCGG  TGTATCTATA  AAGAGAGGG   GTG TTT GTG GCA AGC AAG CAG GCT       1193
                                    Val Phe Val Ala Ser Lys Gln Ala
                                     1              5

GAT GAA CAA AAA AAG CTA GTT ATA GAG CAA GAG GTT CAA AAA CGG CAG           1241
Asp Glu Gln Lys Lys Leu Val Ile Glu Gln Glu Val Gln Lys Arg Gln
     10              15                  20

TTT CAA AAA ATA GAA GAA CTT AAA ACA GAC ATG CAA AAA GGT ATT AAT          1289
Phe Gln Lys Ile Glu Glu Leu Lys Thr Asp Met Gln Lys Gly Ile Asn
 25                  30                  35                  40

CCC TTT TTT AAA GTC TTG TTT GAT GGG GGG AAT AGG TTG TTT GGT TTC          1337
Pro Phe Phe Lys Val Leu Phe Asp Gly Gly Asn Arg Leu Phe Gly Phe
             45                  50                  55

CCT GAA ACT TTT ATT TAT TCC TCC ATA TTT ATA TTG TTT GTA ACA ATT          1385
Pro Glu Thr Phe Ile Tyr Ser Ser Ile Phe Ile Leu Phe Val Thr Ile
                 60                  65                  70

GTA TTA TCT GTT ATT CTT TTT CAA GCC TAT GAA CCT GTT TTG ATT GTA          1433
Val Leu Ser Val Ile Leu Phe Gln Ala Tyr Glu Pro Val Leu Ile Val
         75                  80                  85

GCG ATT GTT ATT GTG CTT GTA GCT CTT GGA TTC AAG AAA GAT TAC AGG          1481
```

```
Ala  Ile  Val  Ile  Val  Leu  Val  Ala  Leu  Gly  Phe  Lys  Lys  Asp  Tyr  Arg
      90                  95                      100

CTT  TAT  CAA  AGA  ATG  GAG  CGA  GCG  ATG  AAA  TTT  AAA  AAA  CCT  TTT  TTG        1529
Leu  Tyr  Gln  Arg  Met  Glu  Arg  Ala  Met  Lys  Phe  Lys  Lys  Pro  Phe  Leu
105                      110                      115                      120

TTT  AAG  GGC  GTG  AAA  AAC  AAA  GCG  TTC  ATG  AGC  ATT  TTT  TCC  ATG  AAG        1577
Phe  Lys  Gly  Val  Lys  Asn  Lys  Ala  Phe  Met  Ser  Ile  Phe  Ser  Met  Lys
                         125                      130                      135

CCT  AGT  AAA  GAA  ATG  GCG  AAT  GAC  ATC  CAC  TTA  AAT  CCA  AAC  AGA  GAA        1625
Pro  Ser  Lys  Glu  Met  Ala  Asn  Asp  Ile  His  Leu  Asn  Pro  Asn  Arg  Glu
                140                      145                      150

GAC  AGA  CTT  GTG  AGC  GCT  GCA  AAT  TCC  TAT  CTA  GCG  AAT  AAC  TAT  GAA        1673
Asp  Arg  Leu  Val  Ser  Ala  Ala  Asn  Ser  Tyr  Leu  Ala  Asn  Asn  Tyr  Glu
          155                      160                      165

TGT  TTT  TTA  GAT  GAT  GGG  GTG  ATC  CTT  ACT  AAC  AAC  TAT  TCT  CTT  TTA        1721
Cys  Phe  Leu  Asp  Asp  Gly  Val  Ile  Leu  Thr  Asn  Asn  Tyr  Ser  Leu  Leu
170                      175                      180

GGC  ACA  ATC  AAA  TTG  GGG  GGC  ATT  GAT  TTT  TTA  ACC  ACT  TCC  AAA  AAA        1769
Gly  Thr  Ile  Lys  Leu  Gly  Gly  Ile  Asp  Phe  Leu  Thr  Thr  Ser  Lys  Lys
185                      190                      195                      200

GAT  CTC  ATA  GAG  TTA  CAC  GCT  TCT  ATT  TAT  AGC  GTT  TTT  AGG  AAT  TTT        1817
Asp  Leu  Ile  Glu  Leu  His  Ala  Ser  Ile  Tyr  Ser  Val  Phe  Arg  Asn  Phe
                         205                      210                      215

GTT  ACC  CCT  GAA  TTC  AAA  TTT  TAT  TTT  CAC  ACT  ATT  AAA  AAG  AAA  ATC        1865
Val  Thr  Pro  Glu  Phe  Lys  Phe  Tyr  Phe  His  Thr  Ile  Lys  Lys  Lys  Ile
                220                      225                      230

GTT  ATT  GAT  GAA  ACC  AAT  AGG  GAT  TAT  GGT  CTT  ATT  TTT  TCT  AAT  GAT        1913
Val  Ile  Asp  Glu  Thr  Asn  Arg  Asp  Tyr  Gly  Leu  Ile  Phe  Ser  Asn  Asp
          235                      240                      245

TTC  ATG  CGA  GCC  TAT  AAT  GAG  AAG  CAA  AAG  AGA  GAA  AGT  TTT  TAT  GAT        1961
Phe  Met  Arg  Ala  Tyr  Asn  Glu  Lys  Gln  Lys  Arg  Glu  Ser  Phe  Tyr  Asp
250                      255                      260

ATT  AGT  TTT  TAT  CTC  ACC  ATA  GAG  CAA  GAT  TTA  TTA  GAC  ACT  CTC  AAT        2009
Ile  Ser  Phe  Tyr  Leu  Thr  Ile  Glu  Gln  Asp  Leu  Leu  Asp  Thr  Leu  Asn
265                      270                      275                      280

GAA  CCC  GTT  ATG  AAT  AAA  AAG  CAT  TTT  GCA  GAT  AAT  AAT  TTT  GAA  GAG        2057
Glu  Pro  Val  Met  Asn  Lys  Lys  His  Phe  Ala  Asp  Asn  Asn  Phe  Glu  Glu
                         285                      290                      295

TTT  CAA  AGG  ATT  ATT  AGA  GCC  AAG  CTT  GAA  AAC  TTC  AAG  GAT  AGG  ATA        2105
Phe  Gln  Arg  Ile  Ile  Arg  Ala  Lys  Leu  Glu  Asn  Phe  Lys  Asp  Arg  Ile
                300                      305                      310

GAG  CTT  ATA  GAA  GAG  CTA  CTG  AGT  AAA  TAC  CAC  CCC  ACT  AGA  TTG  AAA        2153
Glu  Leu  Ile  Glu  Glu  Leu  Leu  Ser  Lys  Tyr  His  Pro  Thr  Arg  Leu  Lys
          315                      320                      325

GAA  TAC  ACC  AAA  GAT  GGC  ATT  ATT  TAT  TCC  AAA  CAA  TGC  GAG  TTT  TAT        2201
Glu  Tyr  Thr  Lys  Asp  Gly  Ile  Ile  Tyr  Ser  Lys  Gln  Cys  Glu  Phe  Tyr
330                      335                      340

AAT  TTT  TTG  GTG  GGA  ATG  AAT  GAA  GCC  CCT  TTT  ATT  TCG  AAC  CGA  AAA        2249
Asn  Phe  Leu  Val  Gly  Met  Asn  Glu  Ala  Pro  Phe  Ile  Ser  Asn  Arg  Lys
345                      350                      355                      360

GAC  TTG  TAT  CTC  AAA  GAA  AAA  ATG  CAT  GGT  GGG  GTG  AAA  GAA  GTT  TAT        2297
Asp  Leu  Tyr  Leu  Lys  Glu  Lys  Met  His  Gly  Gly  Val  Lys  Glu  Val  Tyr
                         365                      370                      375

TTT  GCT  AAT  AAG  CAT  GGA  AAA  ATC  TTA  AAT  GAC  GAT  TTG  AGT  GAA  AAA        2345
Phe  Ala  Asn  Lys  His  Gly  Lys  Ile  Leu  Asn  Asp  Asp  Leu  Ser  Glu  Lys
                380                      385                      390

TAT  TTT  AGT  GCT  ATT  GAG  ATC  AGT  GAA  TAC  GCC  CCT  AAA  TCA  CAG  AGC        2393
Tyr  Phe  Ser  Ala  Ile  Glu  Ile  Ser  Glu  Tyr  Ala  Pro  Lys  Ser  Gln  Ser
          395                      400                      405

GAT  TTG  TTT  GAT  AAA  ATC  AAC  GCT  CTA  GAC  AGC  GAA  TTT  ATC  TTT  ATG        2441
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Asp | Leu | Phe | Asp | Lys | Ile | Asn | Ala | Leu | Asp | Ser | Glu | Phe | Ile | Phe | Met |      |
|     | 410 |     |     |     | 415 |     |     |     | 420 |     |     |     |     |     |     |      |
| CAT | GCT | TAT | TCG | CCT | AAA | AAC | TCA | CAA | GTT | TTA | AAG | GAC | AAA | CTA | GCT | 2489 |
| His | Ala | Tyr | Ser | Pro | Lys | Asn | Ser | Gln | Val | Leu | Lys | Asp | Lys | Leu | Ala |      |
| 425 |     |     |     | 430 |     |     |     | 435 |     |     |     |     |     |     | 440 |      |
| TTC | ACC | TCT | AGA | AGG | ATT | ATT | ATT | AGT | GGA | GGC | TCC | AAA | GAG | CAA | GGC | 2537 |
| Phe | Thr | Ser | Arg | Arg | Ile | Ile | Ile | Ser | Gly | Gly | Ser | Lys | Glu | Gln | Gly |      |
|     |     |     |     | 445 |     |     |     |     | 450 |     |     |     |     | 455 |     |      |
| ATG | ACT | TTG | GGT | TGC | TTG | AGC | GAA | TTA | GTG | GGT | AAT | GGT | GAT | ATT | ACG | 2585 |
| Met | Thr | Leu | Gly | Cys | Leu | Ser | Glu | Leu | Val | Gly | Asn | Gly | Asp | Ile | Thr |      |
|     |     |     | 460 |     |     |     |     | 465 |     |     |     |     | 470 |     |     |      |
| CTA | GGC | AGT | TAT | GGT | AAT | TCT | TTA | GTG | CTG | TTT | GCT | GAT | AGC | TTT | GAA | 2633 |
| Leu | Gly | Ser | Tyr | Gly | Asn | Ser | Leu | Val | Leu | Phe | Ala | Asp | Ser | Phe | Glu |      |
|     |     | 475 |     |     |     |     | 480 |     |     |     |     | 485 |     |     |     |      |
| AAA | ATG | AAA | CAA | AGC | GTT | AAG | GAA | TGC | GTC | TCG | AGT | CTT | AAC | GCT | AAA | 2681 |
| Lys | Met | Lys | Gln | Ser | Val | Lys | Glu | Cys | Val | Ser | Ser | Leu | Asn | Ala | Lys |      |
|     | 490 |     |     |     | 495 |     |     |     |     | 500 |     |     |     |     |     |      |
| GGT | TTT | TTA | GCC | AAC | GCA | GCG | ACT | TTC | TCT | ATG | GAA | AAT | TAC | TTT | TTT | 2729 |
| Gly | Phe | Leu | Ala | Asn | Ala | Ala | Thr | Phe | Ser | Met | Glu | Asn | Tyr | Phe | Phe |      |
| 505 |     |     |     | 510 |     |     |     |     | 515 |     |     |     |     | 520 |     |      |
| GCC | AAA | CAT | TGC | TCT | TTT | ATC | ACG | CTT | CCT | TTT | ATT | TTT | GAT | GTA | ACT | 2777 |
| Ala | Lys | His | Cys | Ser | Phe | Ile | Thr | Leu | Pro | Phe | Ile | Phe | Asp | Val | Thr |      |
|     |     |     | 525 |     |     |     |     | 530 |     |     |     |     | 535 |     |     |      |
| TCT | AAC | AAT | TTT | GCT | GAT | TTC | ATA | GCG | ATG | AGA | GCG | ATG | AGT | TTT | GAT | 2825 |
| Ser | Asn | Asn | Phe | Ala | Asp | Phe | Ile | Ala | Met | Arg | Ala | Met | Ser | Phe | Asp |      |
|     |     |     | 540 |     |     |     | 545 |     |     |     |     | 550 |     |     |     |      |
| GGC | AAT | CAA | GAC | AAT | AAC | GCT | TGG | GGC | AAT | AGC | GTG | ATG | ACG | CTA | AAA | 2873 |
| Gly | Asn | Gln | Asp | Asn | Asn | Ala | Trp | Gly | Asn | Ser | Val | Met | Thr | Leu | Lys |      |
|     | 555 |     |     |     |     | 560 |     |     |     |     | 565 |     |     |     |     |      |
| AGC | GAG | ATC | AAC | TCG | CCT | TTT | TAT | CTC | AAT | TTC | CAC | ATG | CCT | ACT | GAT | 2921 |
| Ser | Glu | Ile | Asn | Ser | Pro | Phe | Tyr | Leu | Asn | Phe | His | Met | Pro | Thr | Asp |      |
| 570 |     |     |     |     | 575 |     |     |     |     | 580 |     |     |     |     |     |      |
| TTT | GGT | TCA | GCT | TCA | GCA | GGA | CAC | ACT | TTG | ATA | CTT | GGC | TCA | ACC | GGT | 2969 |
| Phe | Gly | Ser | Ala | Ser | Ala | Gly | His | Thr | Leu | Ile | Leu | Gly | Ser | Thr | Gly |      |
| 585 |     |     |     | 590 |     |     |     |     | 595 |     |     |     |     | 600 |     |      |
| TCA | GGT | AAA | ACA | GTG | TTT | ATG | TCC | ATG | ACT | CTA | AAC | GCT | ATG | GGG | CAA | 3017 |
| Ser | Gly | Lys | Thr | Val | Phe | Met | Ser | Met | Thr | Leu | Asn | Ala | Met | Gly | Gln |      |
|     |     |     |     | 605 |     |     |     |     | 610 |     |     |     |     | 615 |     |      |
| TTT | GCT | ATA | ATT | TTC | CTG | CTA | ATG | TCA | GCA | AAG | ACA | AAC | AAA | AGC | CTC | 3065 |
| Phe | Ala | Ile | Ile | Phe | Leu | Leu | Met | Ser | Ala | Lys | Thr | Asn | Lys | Ser | Leu |      |
|     |     |     | 620 |     |     |     |     | 625 |     |     |     |     | 630 |     |     |      |
| ACT | ATG | GTC | TAT | ATG | GAT | AAA | GAT | TAT | GGT | GCT | TAT | GGG | AAT | ATT | GTC | 3113 |
| Thr | Met | Val | Tyr | Met | Asp | Lys | Asp | Tyr | Gly | Ala | Tyr | Gly | Asn | Ile | Val |      |
|     |     | 635 |     |     |     | 640 |     |     |     |     | 645 |     |     |     |     |      |
| GCA | ATG | GGT | GGG | GAG | TAT | GTC | AAG | ATT | GAG | CTA | GGG | ACA | GAT | ACA | GGA | 3161 |
| Ala | Met | Gly | Gly | Glu | Tyr | Val | Lys | Ile | Glu | Leu | Gly | Thr | Asp | Thr | Gly |      |
|     | 650 |     |     |     |     | 655 |     |     |     |     | 660 |     |     |     |     |      |
| TTA | AAT | CCT | TTT | GCT | TGG | GCG | GCT | TGC | GTG | CAA | AAA | ACA | GAT | GCA | ACA | 3209 |
| Leu | Asn | Pro | Phe | Ala | Trp | Ala | Ala | Cys | Val | Gln | Lys | Thr | Asp | Ala | Thr |      |
| 665 |     |     |     |     | 670 |     |     |     |     | 675 |     |     |     |     | 680 |      |
| ATG | GAG | CAA | AAA | CAA | ACG | GCT | ATT | TCT | GTT | GTC | AAA | GAG | CTT | GTG | AAG | 3257 |
| Met | Glu | Gln | Lys | Gln | Thr | Ala | Ile | Ser | Val | Val | Lys | Glu | Leu | Val | Lys |      |
|     |     |     |     | 685 |     |     |     |     | 690 |     |     |     |     | 695 |     |      |
| AAC | CTA | GCG | ACC | AAA | AGC | GAT | GAA | AAA | GAT | GAA | AAT | GGC | AAC | AGC | GTC | 3305 |
| Asn | Leu | Ala | Thr | Lys | Ser | Asp | Glu | Lys | Asp | Glu | Asn | Gly | Asn | Ser | Val |      |
|     |     |     | 700 |     |     |     |     | 705 |     |     |     |     | 710 |     |     |      |
| TCT | TTT | AGC | CTA | GCC | GAT | TCT | AAC | ACG | CTT | GCA | GCG | GCA | GTA | ACC | AAC | 3353 |
| Ser | Phe | Ser | Leu | Ala | Asp | Ser | Asn | Thr | Leu | Ala | Ala | Ala | Val | Thr | Asn |      |
|     |     | 715 |     |     |     |     | 720 |     |     |     |     | 725 |     |     |     |      |
| CTT | ATC | ACA | GGA | GAT | ATG | AAC | CTA | GAT | TAT | CCC | ATC | ACT | CAA | CTT | ATT | 3401 |

```
Leu Ile Thr Gly Asp Met Asn Leu Asp Tyr Pro Ile Thr Gln Leu Ile
    730                 735                 740

AAC GCT TTT GGA AAA GAC CAC AAT GAT CCT AAT GGG CTT GTC GCG CGA        3449
Asn Ala Phe Gly Lys Asp His Asn Asp Pro Asn Gly Leu Val Ala Arg
745                 750                 755                 760

TTA GCG CCT TTT TGC AAA TCA ACC AAT GGT GAA TTT CAA TGG CTT TTT        3497
Leu Ala Pro Phe Cys Lys Ser Thr Asn Gly Glu Phe Gln Trp Leu Phe
                765                 770                 775

GAT AAT AAA GCA ACA GAT CGC TTA GAT TTT TCA AAA ACG ATT ATT GGC        3545
Asp Asn Lys Ala Thr Asp Arg Leu Asp Phe Ser Lys Thr Ile Ile Gly
            780                 785                 790

GTT GAT GGG TCA AGT TTC TTA GAC AAT AAT GAT GTT TCG CCC TTT ATT        3593
Val Asp Gly Ser Ser Phe Leu Asp Asn Asn Asp Val Ser Pro Phe Ile
        795                 800                 805

TGT TTT TAC CTT TTC GCT CGT ATC CAA GAG GCA ATG GAT GGG CGT AGA        3641
Cys Phe Tyr Leu Phe Ala Arg Ile Gln Glu Ala Met Asp Gly Arg Arg
    810                 815                 820

TTT GTC TTA GAT ATT GAT GAA GCG TGG AAA TAC TTA AGC GAT CCA AAG        3689
Phe Val Leu Asp Ile Asp Glu Ala Trp Lys Tyr Leu Ser Asp Pro Lys
825                 830                 835                 840

GTC GCT TAT TTT GTA AGA GAC ATG CTA AAA ACC GCA AGA AAA GAA ACG        3737
Val Ala Tyr Phe Val Arg Asp Met Leu Lys Thr Ala Arg Lys Glu Thr
                845                 850                 855

CTA TTG TTA GAC TTG CAA CCC AAA GCA TCA CTG ATC TTT TGG CTT GCC        3785
Leu Leu Leu Asp Leu Gln Pro Lys Ala Ser Leu Ile Phe Trp Leu Ala
            860                 865                 870

CTA TTG CTG ATA CGA TTA GAG AAC AAT GCC CTA CAA AGA TTT TTT            3830
Leu Leu Leu Ile Arg Leu Glu Asn Asn Ala Leu Gln Arg Phe Phe
        875                 880                 885

TGAGAAACGA TGGGGGTAAT CTTTCTGATT ACCAAGATT AGCCAATGTT ACAGAAAAAG       3890

AATTTGAAAT CATCACTAAG GGGCTAGATA GGAAAATCCT CTACAAACAG GACGGAAGCC      3950

CTAGCGTTAT CGCTAGTTTT AATTTGAGAG GCGCTTCCT                             3989
```

( 2 ) INFORMATION FOR SEQ ID NO:4:

( i ) SEQUENCE CHARACTERISTICS:
        ( A ) LENGTH: 887 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Val Phe Val Ala Ser Lys Gln Ala Asp Glu Gln Lys Lys Leu Val Ile
1               5                   10                  15

Glu Gln Glu Val Gln Lys Arg Gln Phe Gln Lys Ile Glu Glu Leu Lys
                20                  25                  30

Thr Asp Met Gln Lys Gly Ile Asn Pro Phe Phe Lys Val Leu Phe Asp
            35                  40                  45

Gly Gly Asn Arg Leu Phe Gly Phe Pro Glu Thr Phe Ile Tyr Ser Ser
        50                  55                  60

Ile Phe Ile Leu Phe Val Thr Ile Val Leu Ser Val Ile Leu Phe Gln
65              70                  75                  80

Ala Tyr Glu Pro Val Leu Ile Val Ala Ile Val Ile Val Leu Val Ala
                85                  90                  95

Leu Gly Phe Lys Lys Asp Tyr Arg Leu Tyr Gln Arg Met Glu Arg Ala
            100                 105                 110

Met Lys Phe Lys Lys Pro Phe Leu Phe Lys Gly Val Lys Asn Lys Ala
        115                 120                 125
```

```
Phe Met Ser Ile Phe Ser Met Lys Pro Ser Lys Glu Met Ala Asn Asp
    130             135             140
Ile His Leu Asn Pro Asn Arg Glu Asp Arg Leu Val Ser Ala Ala Asn
145             150             155                 160
Ser Tyr Leu Ala Asn Asn Tyr Glu Cys Phe Leu Asp Asp Gly Val Ile
            165             170             175
Leu Thr Asn Asn Tyr Ser Leu Leu Gly Thr Ile Lys Leu Gly Gly Ile
        180             185             190
Asp Phe Leu Thr Thr Ser Lys Lys Asp Leu Ile Glu Leu His Ala Ser
        195             200             205
Ile Tyr Ser Val Phe Arg Asn Phe Val Thr Pro Glu Phe Lys Phe Tyr
    210             215             220
Phe His Thr Ile Lys Lys Lys Ile Val Ile Asp Glu Thr Asn Arg Asp
225             230             235                 240
Tyr Gly Leu Ile Phe Ser Asn Asp Phe Met Arg Ala Tyr Asn Glu Lys
            245             250             255
Gln Lys Arg Glu Ser Phe Tyr Asp Ile Ser Phe Tyr Leu Thr Ile Glu
            260             265             270
Gln Asp Leu Leu Asp Thr Leu Asn Glu Pro Val Met Asn Lys Lys His
        275             280             285
Phe Ala Asp Asn Asn Phe Glu Glu Phe Gln Arg Ile Ile Arg Ala Lys
290             295             300
Leu Glu Asn Phe Lys Asp Arg Ile Glu Leu Ile Glu Glu Leu Leu Ser
305             310             315                 320
Lys Tyr His Pro Thr Arg Leu Lys Glu Tyr Thr Lys Asp Gly Ile Ile
            325             330             335
Tyr Ser Lys Gln Cys Glu Phe Tyr Asn Phe Leu Val Gly Met Asn Glu
            340             345             350
Ala Pro Phe Ile Ser Asn Arg Lys Asp Leu Tyr Leu Lys Glu Lys Met
        355             360             365
His Gly Gly Val Lys Glu Val Tyr Phe Ala Asn Lys His Gly Lys Ile
    370             375             380
Leu Asn Asp Asp Leu Ser Glu Lys Tyr Phe Ser Ala Ile Glu Ile Ser
385             390             395                 400
Glu Tyr Ala Pro Lys Ser Gln Ser Asp Leu Phe Asp Lys Ile Asn Ala
            405             410             415
Leu Asp Ser Glu Phe Ile Phe Met His Ala Tyr Ser Pro Lys Asn Ser
            420             425             430
Gln Val Leu Lys Asp Lys Leu Ala Phe Thr Ser Arg Arg Ile Ile Ile
        435             440             445
Ser Gly Gly Ser Lys Glu Gln Gly Met Thr Leu Gly Cys Leu Ser Glu
    450             455             460
Leu Val Gly Asn Gly Asp Ile Thr Leu Gly Ser Tyr Gly Asn Ser Leu
465             470             475                 480
Val Leu Phe Ala Asp Ser Phe Glu Lys Met Lys Gln Ser Val Lys Glu
            485             490             495
Cys Val Ser Ser Leu Asn Ala Lys Gly Phe Leu Ala Asn Ala Ala Thr
            500             505             510
Phe Ser Met Glu Asn Tyr Phe Phe Ala Lys His Cys Ser Phe Ile Thr
        515             520             525
Leu Pro Phe Ile Phe Asp Val Thr Ser Asn Asn Phe Ala Asp Phe Ile
        530             535             540
Ala Met Arg Ala Met Ser Phe Asp Gly Asn Gln Asp Asn Asn Ala Trp
```

```
545                       550                       555                       560
Gly  Asn  Ser  Val  Met  Thr  Leu  Lys  Ser  Glu  Ile  Asn  Ser  Pro  Phe  Tyr
                    565                      570                      575

Leu  Asn  Phe  His  Met  Pro  Thr  Asp  Phe  Gly  Ser  Ala  Ser  Ala  Gly  His
               580                      585                     590

Thr  Leu  Ile  Leu  Gly  Ser  Thr  Gly  Ser  Gly  Lys  Thr  Val  Phe  Met  Ser
               595                      600                     605

Met  Thr  Leu  Asn  Ala  Met  Gly  Gln  Phe  Ala  Ile  Ile  Phe  Leu  Leu  Met
     610                      615                     620

Ser  Ala  Lys  Thr  Asn  Lys  Ser  Leu  Thr  Met  Val  Tyr  Met  Asp  Lys  Asp
625                      630                      635                      640

Tyr  Gly  Ala  Tyr  Gly  Asn  Ile  Val  Ala  Met  Gly  Gly  Glu  Tyr  Val  Lys
                    645                      650                     655

Ile  Glu  Leu  Gly  Thr  Asp  Thr  Gly  Leu  Asn  Pro  Phe  Ala  Trp  Ala  Ala
               660                      665                     670

Cys  Val  Gln  Lys  Thr  Asp  Ala  Thr  Met  Glu  Gln  Lys  Gln  Thr  Ala  Ile
               675                      680                     685

Ser  Val  Val  Lys  Glu  Leu  Val  Lys  Asn  Leu  Ala  Thr  Lys  Ser  Asp  Glu
     690                      695                     700

Lys  Asp  Glu  Asn  Gly  Asn  Ser  Val  Ser  Phe  Ser  Leu  Ala  Asp  Ser  Asn
705                      710                      715                      720

Thr  Leu  Ala  Ala  Ala  Val  Thr  Asn  Leu  Ile  Thr  Gly  Asp  Met  Asn  Leu
                    725                      730                     735

Asp  Tyr  Pro  Ile  Thr  Gln  Leu  Ile  Asn  Ala  Phe  Gly  Lys  Asp  His  Asn
               740                      745                     750

Asp  Pro  Asn  Gly  Leu  Val  Ala  Arg  Leu  Ala  Pro  Phe  Cys  Lys  Ser  Thr
               755                      760                     765

Asn  Gly  Glu  Phe  Gln  Trp  Leu  Phe  Asp  Asn  Lys  Ala  Thr  Asp  Arg  Leu
     770                      775                     780

Asp  Phe  Ser  Lys  Thr  Ile  Ile  Gly  Val  Asp  Gly  Ser  Ser  Phe  Leu  Asp
785                      790                      795                      800

Asn  Asn  Asp  Val  Ser  Pro  Phe  Ile  Cys  Phe  Tyr  Leu  Phe  Ala  Arg  Ile
                    805                      810                     815

Gln  Glu  Ala  Met  Asp  Gly  Arg  Arg  Phe  Val  Leu  Asp  Ile  Asp  Glu  Ala
               820                      825                     830

Trp  Lys  Tyr  Leu  Ser  Asp  Pro  Lys  Val  Ala  Tyr  Phe  Val  Arg  Asp  Met
               835                      840                     845

Leu  Lys  Thr  Ala  Arg  Lys  Glu  Thr  Leu  Leu  Leu  Asp  Leu  Gln  Pro  Lys
     850                      855                     860

Ala  Ser  Leu  Ile  Phe  Trp  Leu  Ala  Leu  Leu  Leu  Ile  Arg  Leu  Glu  Asn
865                      870                      875                      880

Asn  Ala  Leu  Gln  Arg  Phe  Phe
                    885
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TGAAGGTCGG AGTCAACGGA TTTGGT        26

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CATGTTGAGG TCCACCAC         18

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATGACTTCCA AGCTGGCCGT GGC         23

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TCTCAGCCCT CTTCAAAAAC TTCTC         25